United States Patent
Ayliffe

(10) Patent No.: US 8,329,437 B1
(45) Date of Patent: Dec. 11, 2012

(54) DISPOSABLE PARTICLE COUNTER CARTRIDGE

(75) Inventor: Harold E. Ayliffe, Woodinville, WA (US)

(73) Assignee: E.I. Spectra, LLC, Hailey, ID (US)

( * ) Notice: Subject to any disclaimer, the term of this patent is extended or adjusted under 35 U.S.C. 154(b) by 110 days.

(21) Appl. No.: 12/639,095

(22) Filed: Dec. 16, 2009

Related U.S. Application Data

(62) Division of application No. 11/193,984, filed on Jul. 29, 2005, now abandoned.

(60) Provisional application No. 60/592,350, filed on Jul. 29, 2004.

(51) Int. Cl.
*C12N 13/00* (2006.01)

(52) U.S. Cl. ............... 435/173.9; 435/287.1; 422/68.1; 422/73

(58) Field of Classification Search ............ 435/287.1, 435/2, 325, 173.9, 261; 257/40; 422/73, 422/68.1, 82.01
See application file for complete search history.

(56) References Cited

U.S. PATENT DOCUMENTS

| | | |
|---|---|---|
| 5,376,878 A | 12/1994 | Fisher |
| 6,169,394 B1 | 1/2001 | Frazier et al. |
| 6,382,228 B1 | 5/2002 | Cabuz et al. |
| 6,426,615 B1 | 7/2002 | Mehta |
| 6,440,725 B1 | 8/2002 | Pourahmadi et al. |
| 6,454,945 B1 | 9/2002 | Weigl et al. |
| 6,473,551 B2 | 10/2002 | Norwood et al. |
| 6,488,896 B2 | 12/2002 | Weigl et al. |
| 6,656,431 B2 | 12/2003 | Holl et al. |
| 6,703,819 B2 | 3/2004 | Gascoyne et al. |
| 6,794,877 B2 | 9/2004 | Blomberg et al. |
| 2002/0117517 A1 | 8/2002 | Unger et al. |
| 2004/0151629 A1 | 8/2004 | Pease et al. |
| 2005/0054078 A1 | 3/2005 | Miller et al. |
| 2005/0118705 A1 | 6/2005 | Rabbitt et al. |

*Primary Examiner* — Michael Hobbs
(74) *Attorney, Agent, or Firm* — Brian C. Trask

(57) ABSTRACT

A single-use disposable cartridge and reusable interrogation platform for interrogating particles in a fluid carrier medium. The cartridge includes a micro-electro-mechanical system (MEMS) embodied in a chip to perform electrical property interrogations of fluid flowing in a micro channel. Desirably, the microchannel is sized to cause single-file particle flow past a sensor portion of the MEMS chip.

10 Claims, 24 Drawing Sheets

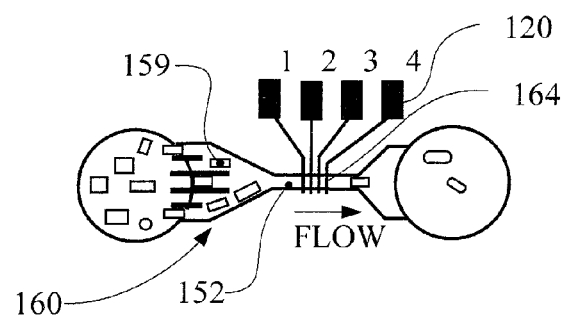
FIG. 9
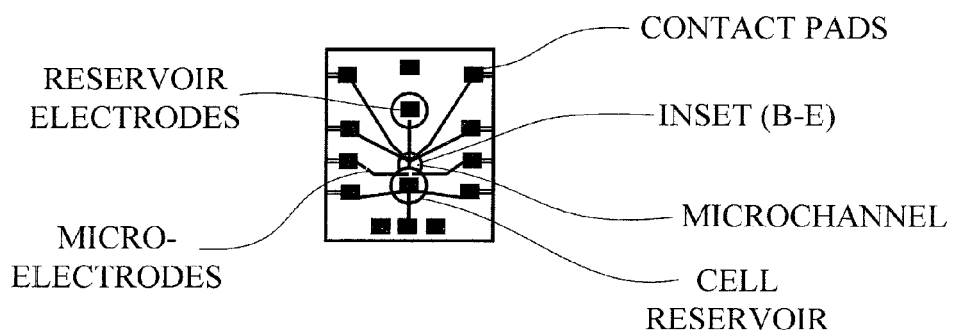
FIG. 10A
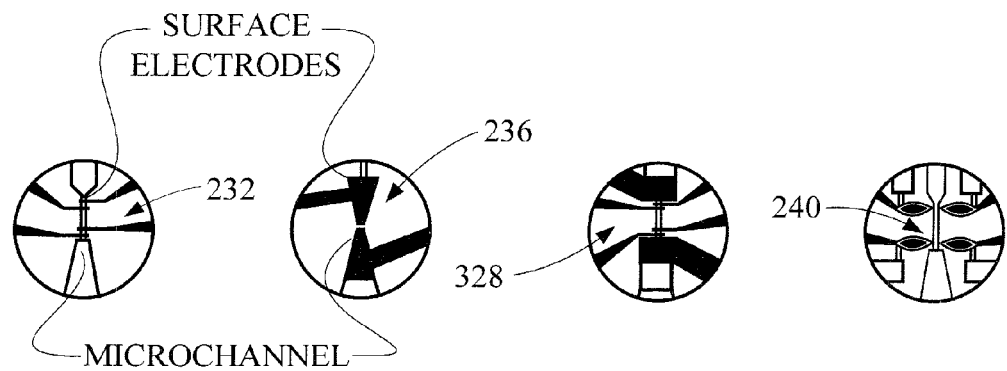
| TWIN SURFACE ELECTRODES | COULTER STYLE ELECTRODES | TWIN COULTER COMBINATION | DOUBLE SIDE ELECTRODES |
|---|---|---|---|
| FIG. 10B | FIG. 10C | FIG. 10D | FIG. 10E |

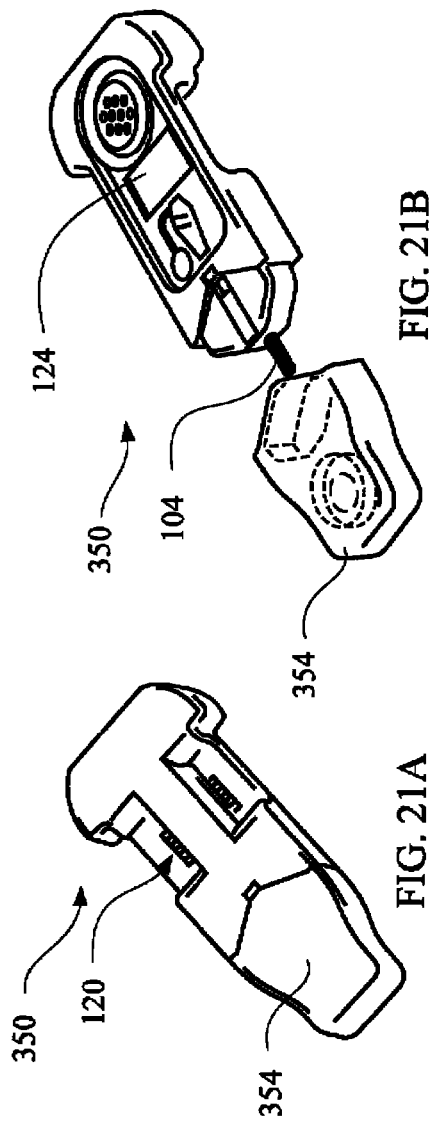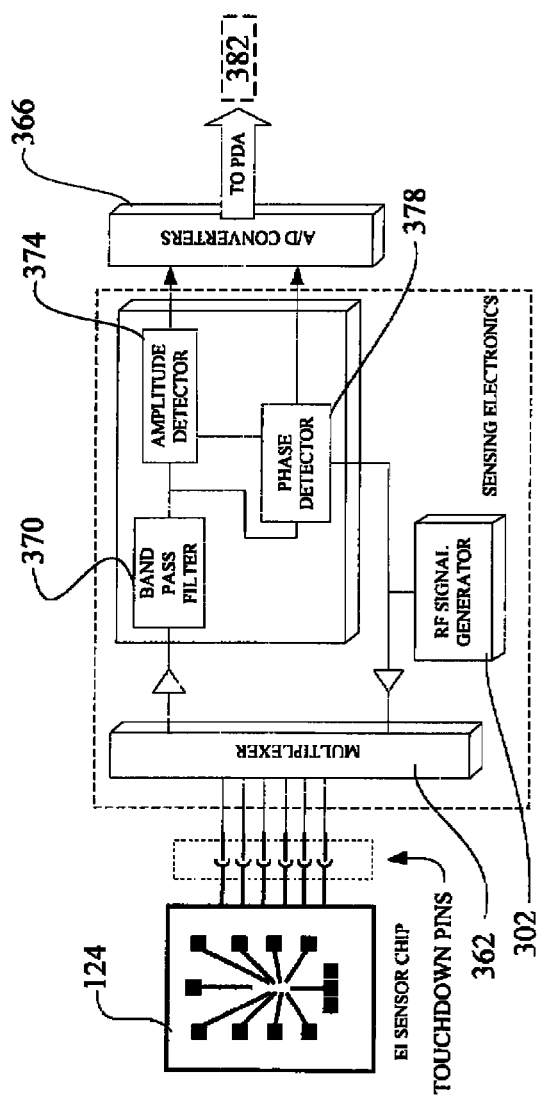

DISPOSABLE PARTICLE COUNTER CARTRIDGE

RELATED APPLICATIONS

This application is a divisional of U.S. application Ser. No. 11/193,984 Jul. 29, 2005 now abandoned, and claims the benefit under 35 U.S.C. 119(e) of the filing date of Provisional Application Ser. No. 60/592,350, filed Jul. 29, 2004 for "DISPOSABLE COMPLETE BLOOD-CELL COUNT DEVICE", the disclosures of which are incorporated as a portion of this disclosure as though set forth in their entirety herein.

BACKGROUND

1. Field of the Invention

The invention relates generally to electronic sensors, and particularly to such sensors adapted to electrically interrogate small particles suspended in a fluid carrier medium.

2. State of the Art

Pioneering work in particle detection by measuring impedance deviation caused by particles flowing through a small aperture between two containers of conductive fluids is disclosed in U.S. Pat. No. 2,656,508 to W. H, Coulter. The inventor's name is now associated with the principle of particles causing a change in electric impedance as they occlude a portion of the aperture. Since publication of his patent, considerable effort has been devoted to developing and refining sensing devices operating under the Coulter principle. Relevant US patents include U.S. Pat. No. 5,376,878 to Fisher, U.S. Pat. No. 6,703,819 to Gascoyne et al., U.S. Pat. No. 6,437,551 to Krulevitch et al., U.S. Pat. No. 6,426,615 to Mehta, U.S. Pat. No. 6,169,394 to Frazier et al., U.S. Pat. No. 6,454,945 and U.S. Pat. No. 6,488,896 to Weigl et al., U.S. Pat. No. 6,656,431 to Holl et al., and U.S. Pat. No. 6,794,877 to Blomberg et al. patent application 2002/117,517 to Unger et al. is also relevant. Each above-referenced document is hereby incorporated by reference, as though set forth herein in their entireties, for their disclosures of technology and various sensor arrangements.

While considerable progress has been made in sensor technology, room remains for improvement to sensors adapted for interrogating particles in conductive fluid that are low in cost, permit sample manipulation, and/or ensure accurate selection of a sample volume. It would be an improvement to provide a sensitive and accurate sensor embodied on a cartridge that is sufficiently low in cost to permit its disposal after a single use. It would be another improvement to provide such a cartridge permitting selection of a defined sample volume. A further improvement would provide a cartridge including bubble detecting and removing structure. A still further improvement would provide such a cartridge including reagents disposed to interact with the sample fluid to permit manipulation of a sample, such as diluting, washing, or reacting. A still further improvement would provide such a cartridge that is additionally structured to permit separation of selected particles from the population introduced as a "raw" sample.

BRIEF SUMMARY OF THE INVENTION

The present invention provides an apparatus and methods for analyzing fluid samples including particles suspended in a carrier fluid. In general, embodiments of the invention may be used in analyses involving numerical evaluation or particle size distribution for a particle-bearing fluid. Nonlimiting examples of fluid samples within contemplation for interrogation by embodiments structured according to the instant invention include whole blood, portions of blood including serum, semen, and milk.

An apparatus constructed according to certain principles of the invention desirably includes an analysis cartridge that is sufficiently simple and inexpensive to permit its disposal subsequent to a single use. A preferred cartridge has a small form-factor to reduce required storage volume and constituent material cost. One convenient size for a cartridge is about the size of a book of paper matches. The cartridge may be coupled with a reusable interrogation platform to perform an electrically-based analysis on the fluid sample.

One embodiment of the invention provides a low-cost, disposable, single-use cartridge operable to perform a complete blood-cell count (CBC) by discriminating between certain cell morphological types. Sometimes, devices structured according to the instant invention may be used in combination with bound markers, such as latex or magnetic beads. Such markers may operate under some sort of discriminatory mechanism or process (such as antigen-antibody binding), to permit binding with only certain cell types. The attached beads or markers can be used to pull targeted cells out of the blood (or other fluid sample), as a method of purification. The "purified" or concentrated cells can then be counted in an embodiment of the present invention. Alternatively, the device may be used as a detector for the combined particles and markers.

Beads attached to cells may be used to aid in specific cell discrimination amongst cells that lack a bound bead. One test performed on blood samples using bound beads is characterized as an absolute CD4+ white blood cell count. The CD4+ white blood cells (WBC)s are white blood cells that express the CD4+ antibody on their membrane and play a key role in the immune system. Embodiments of the invention may be used for counting just the WBCs (non-labeled) with the CD8 labeled cells (latex beads attached). Another example would be to aid in performing a WBC differential analysis using the beads attached to specific white cells. Latex beads are preferred in this method because they can be manufactured to be neutrally buoyant in the dilutent.

An interrogation platform generally includes alignment structure (such as a socket) adapted to receive a cartridge in an installed substantially fixed interrogation orientation and to resist installation of the cartridge in another orientation. Preferred embodiments also include biased retaining structure to hold the cartridge in an installed position. The platform typically houses a fluid motive source, and on-board electronics adapted to collect electrically-based property data responsive to stimulus applied to certain electrodes associated with a cartridge. A portion of the on-board electronics includes a plurality of electrical contacts individually configured for electrical coupling with electrical contact pads carried by a cartridge.

A cartridge includes fluid receiving structure arranged to provide fluid communication of a fluid sample through a channel to a waste reservoir. The channel includes an interrogation portion passing through a micro-electro-mechanical-system (MEMS) chip carried by the cartridge. Desirably, the interrogation portion includes a microchannel sized to cause single-file particle flow past a sensor portion of the MEMS chip. A plurality of aforementioned electrical contact pads carried by the cartridge each are disposed in electrical communication with a selected electrode disposed in association with the interrogation portion. Desirably, connection structure, disposed in fluid communication with the channel through the cartridge, is arranged to couple with a motive source associated with the platform. One operable motive source includes a vacuum source, although fluid may also be pumped, or otherwise urged, through a cartridge. Typically, a hydrophobic membrane barrier is disposed in association with the waste reservoir to permit evacuation of air from the cartridge along a vent path while resisting escape of fluid from the cartridge.

Certain operable cartridges are structured and arranged to perform a plurality of simultaneous parallel electrically-based interrogations on divided subportions of a fluid sample. In such case, each of the divided subportions is urged for flow past a different sensing structure carried on the MEMS chip. Other operable cartridges are structured and arranged to perform electrically-based serial analyses of a fluid sample by permitting manipulation of the fluid sample operably to hold-back a first subset of particles for analysis subsequent to analysis of a second subset of particles.

A preferred MEMS chip includes a first stimulated electrode disposed on a first side of a barrier element and arranged to contact test fluid upstream from a detection zone of the channel. A second stimulated electrode is disposed on a second side of the barrier element and arranged to contact test fluid downstream from the detection zone. A first detection electrode is disposed sandwiched in the barrier element between first and second layers of substantially dielectric material effective to resist electrical communication between each of the first detection electrode, the first stimulated electrode, and the second stimulated electrode. A first conduit portion of the channel provides a flow path through the barrier element and the first detection electrode such that a fluid-contacting area of the first detection electrode circumscribes the first conduit. The first conduit is therefore arranged to provide an electrical continuity between the first stimulated electrode, the first detection electrode, and the second stimulated electrode via electrically conductive liquid communicating through the first conduit.

Sometimes, the MEMS chip may include a second conduit forming sensor in a second fluid flow path that is hydraulically in parallel to the first flow path through the barrier element. Such second conduit passes through a second detection electrode so that a fluid-contacting area of the second detection electrode circumscribes the second conduit. Furthermore, the second detection electrode is also disposed sandwiched in the barrier element between the first and second layers of dielectric material effective to resist electrical communication between each of the first detection electrode, the second detection electrode, the first stimulated electrode, and the second stimulated electrode. The second conduit also provides an electrical continuity between the first stimulated electrode, the second detection electrode, and the second stimulated electrode via electrically conductive liquid communicating through the second conduit. Preferred embodiments of MEMS chips may include a plurality of such hydraulically parallel sensors.

Certain other operable MEMS chips may include a plurality of sensors arranged along a conduit in series. In such case, and with respect to the aforementioned first flow path, a downstream detection electrode may be disposed sandwiched in the barrier element between the second layer and a third layer of substantially dielectric material effective to resist electrical communication between the first detection electrode and the downstream detection electrode. The first conduit may be characterized as passing in series from the first detection electrode through the downstream detection electrode such that a fluid-contacting area of the downstream detection electrode circumscribes the first conduit. In such a configurations, the first conduit provides an electrical continuity between the first stimulated electrode, the first detection electrode, the downstream detection electrode, and the second stimulated electrode via electrically conductive liquid communicating through the first conduit.

Another operable MEMS chip includes a substantially dielectric substrate, a plurality of electrodes disposed in spaced apart relation on a surface of that substrate, and a machinable layer disposed over those electrodes and substrate. The machinable layer is typically etched, or otherwise machined, to form a fluid entrance and a fluid exit coupled in fluid communication through a fluid conduit forming a portion of the aforementioned channel through the cartridge. The fluid conduit may be characterized as forming a flow path along an axis between the fluid entrance and the fluid exit. Desirably, a cross-section of the flow path is sized to cause single-file flow of blood cells along the axis and through a portion of the conduit. A sensor portion of the MEMS chip includes a plurality of electrodes disposed in series along a floor of the conduit at a plurality of axially spaced apart locations, each such electrode being disposed substantially on only one side of a cross-section through the channel. The electrodes make contact with fluid in the fluid conduit as the fluid is urged therethrough.

Certain cartridges also include a reagent reservoir adapted to hold a reagent confined in a rupturable container. Generally, an outlet of that reagent reservoir is disposed in association with the cartridge's channel at a location upstream of the MEMS chip. Preferred embodiments include a puncture structure arranged in cooperation with the rupturable container operably to release reagent for flow through the outlet and into the channel. Regardless of its confinement arrangement with respect to a cartridge, reagents may be diluents, lysing agents, detergents, saline solutions, and water. A workable reagent may include antigen-bound particles. Certain such particles may be embodied as latex beads, and/or magnetic particles.

Sometimes, a cartridge further carries sample selection structure, such as selection structure arranged to define a chamber in which to select a known volume of the sample for processing. One such cartridge includes such a chamber formed between a first valve and a second valve. The valves are separated by a sample-selection length of the channel defining a selection chamber having a known volume. An alternative selection chamber can be formed as a bore through a valve stem. An overflow reservoir may be disposed for interruptible fluid communication with the selection chamber, and can be employed to ensure complete filling of the selection chamber. Desirably, a hydrophobic membrane barrier is disposed in association with the overflow reservoir to permit evacuation of air from the overflow reservoir while resisting escape of fluid. A mixing reservoir can be disposed downstream of the second valve for intermittent fluid communication with the selection chamber. In such case, its fluid outlet is generally upstream of the MEMS chip. Conveniently, a hydrophobic membrane barrier may also be disposed in association with the mixing reservoir to permit evacuation of air from the mixing reservoir while resisting escape of fluid.

A cartridge may further include bubble indication structure. One operable bubble indicator includes a first reference electrode disposed to contact fluid at a first reference location in the cartridge's channel. The first reference electrode is established in electrical communication with a first reference contact pad carried by the cartridge. A second reference electrode is positioned to contact fluid downstream of the first reference location and is placed in electrical communication with a second reference contact pad. The interrogation platform is cooperatingly structured to interrogate electrical impedance between the first and second reference contact pads to infer presence or absence of bubbles between the first and second reference electrodes.

Certain desirable cartridges further include bubble removal structure configured and arranged to remove entrained gas bubbles from at least part of the fluid sample. One exemplary bubble removal structure includes a hydrophobic membrane arranged to form a wall of a degassing chamber in which to hold at least part of the fluid sample. The membrane permits evacuation of entrained gas from the fluid while resisting escape of fluid. Such bubble remover can be associated with any portion of the channel through the cartridge. Preferably, a bubble remover is associated with one or more chambers, such as the sample selection chamber.

Apparatus constructed according to certain principles of the invention may be used in a method for interrogating particles in a known volume of fluid using an electrical property-detecting sensor contained in a single-use, disposable cartridge with an interrogation platform structured to couple with the cartridge. One such method includes the steps of: loading a sample of fluid into the cartridge; urging a quantity of the sample into a degassing chamber defining a known volume; applying a reduced pressure to a portion of a gas permeable wall of the degassing chamber for a period of time effective to cause migration of gas bubbles from said quantity through the wall to form a known and degassed volume of test fluid; urging the known and degassed volume of test fluid to flow past the sensor for interrogation by the platform; and then, disposing of the cartridge.

Apparatus constructed according to certain principles of the invention may also be used in a method for performing a serial analysis on first and second subsets of particles in a fluid sample using an electrical property sensor housed in a single-use, disposable cartridge with an interrogation platform structured to couple with the cartridge. One exemplary such method includes the steps of: loading a sample of fluid into the cartridge; urging a quantity of the sample into a mixing chamber disposed in the cartridge; applying one or more reagent to the quantity effective to form at least two subsets of particles; applying a force effective to restrain movement of a first subset of particles from the mixing chamber; urging a second subset of particles to flow past the sensor for interrogation by the platform; subsequently urging the first subset of particles to flow past a sensor for interrogation by the platform; and then, disposing of the cartridge. In one use where the sample comprises whole blood, one step of the method may include mixing a quantity of antigen-bound magnetic beads with the sample operably to bind the beads to certain white blood cells. Furthermore, another step of the method may include applying a magnetic field to the magnetic beads to restrain their movement. Sometimes, a method of use of certain embodiments of the invention may include the step of adjusting structure associated with the cartridge to cause flow of the first subset of particles for analysis through a second sensor that is differently structured from the first sensor.

BRIEF DESCRIPTION OF THE DRAWINGS

In the drawings, which illustrate what are currently considered to be the best modes for carrying out the invention:

FIG. 9 is a top view of an alternative arrangement for structure of a MEMS chip;

FIG. 10A is a top view of a second alternative arrangement for structure that may be included on a MEMS chip according to certain principles of the invention;

FIGS. 10B-E illustrate alternative electrode configurations workable in certain embodiments of the invention, disposed in an interrogation channel as indicated in the circled portion of the device of FIG. 10A;

FIGS. 21A and B illustrate an assembled and a partially exploded view of a currently preferred interrogation apparatus adapted as a disposable cartridge for measuring a complete blood-cell count;

FIG. 22 is a schematic illustrating a workable electronic arrangement adapted to interface with the cartridge of FIG. 21;

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of the principles of the present invention, and should not be viewed as narrowing the claims which follow.

For convenience, certain embodiments of the invention may be described with reference to their use as a CBC device. Other embodiments may be described with reference to CD4+ testing. Such description is not intended to limit the scope of the instant invention in any way. It is to be understood that the invention may be used in other applications to qualify or quantify particles in a fluid by interrogating an electric response to a stimulus as the particles are urged past a sensor arrangement of the device. Furthermore, in this disclosure, the term "fluid" is typically used to encompass a fluid mix including a fluid and particles suspended or otherwise distributed in that fluid. It is believed that the absence of particles may logically be adduced in context.

Figure 1:
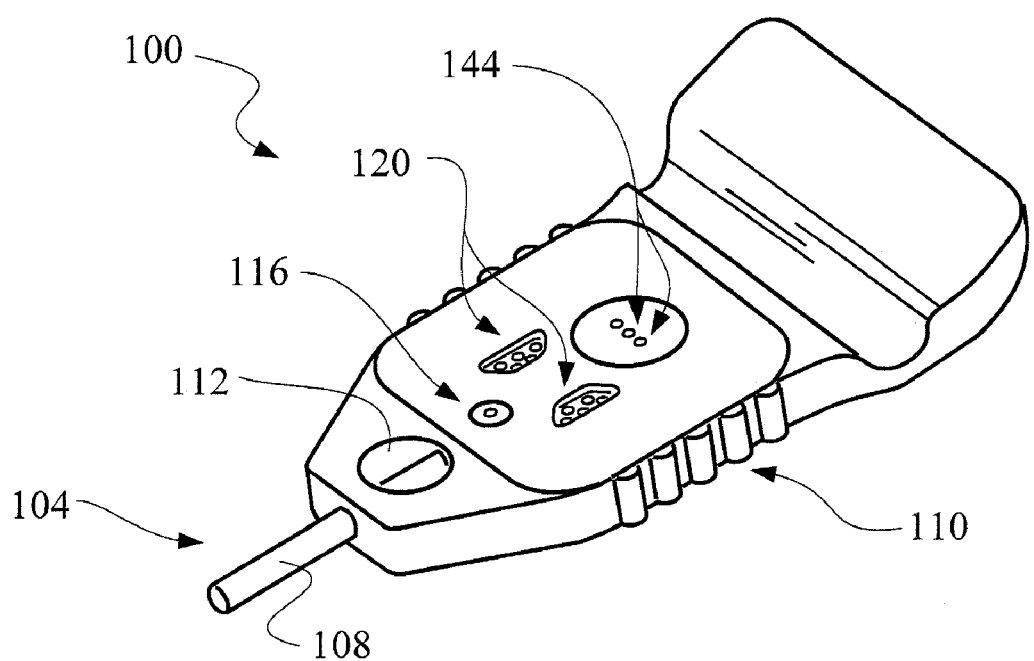
FIG. 1 is a view in perspective of a first preferred embodiment of a CBC device.

With reference now to FIG. 1, a first embodiment of a cartridge structured according to certain principles of the invention, and adapted to perform a CBC test, is indicated generally at 100. Cartridge 100 includes fluid receiving structure, generally indicated at 104, embodied as a capillary tube 108. Tube 108 is adapted to receive a fluid sample by way of capillary action. One such fluid sample may conveniently be acquired from a drop of blood obtained from a prick wound. However, it is within contemplation that an operable receiving structure 104 may be adapted to receive fluid dispensed from a pipette, syringe, or other fluid dispensing structure.

Desirably, cartridge 100 is constructed as such a sufficiently simple and inexpensive device to permit its disposal subsequent to a single use. A preferred cartridge has a small form-factor to reduce its required storage volume and constituent material cost. One convenient size for a cartridge is about the size of a book of paper matches. Certain preferred cartridges may be embodied having a size approximately the size of a thick credit card. Grip-assist structure 110 may be provided to facilitate handling of a cartridge 100.

A window 112 can be provided for a user to visually ensure blood, or other sample fluid, is present inside the cartridge 100. As illustrated, a vent 116 in communication with a sample chamber or channel through the cartridge 100 may be included to assist fluid flow from an external fluid source, through an entrance orifice, and into the device 100. Such vent 116, if present, can typically be occluded subsequent to charging the CBC device's sample-holding reservoir.

One or more vents, such as vent 116, can be disposed at selected fluid-flow control points along a flow channel through a cartridge, such as a cartridge 100. Such vents may be opened and closed to provide a convenient control arrangement, in cooperation with a pump arrangement, such as a low pressure or vacuum source coupled to the vent opening, to urge selective flow of the sample through the cartridge. It is also within contemplation that a fluid sample may be pressurized to cause fluid flow, in which case valves and vents may be used to control such flow. It is generally desirable to operably associate a hydrophobic membrane with a vent to permit evacuation of gasses from the cartridge, and to resist escape of fluids from inside the cartridge. A currently preferred hydrophobic membrane includes polytetrafluoroethylene (PTFE), although gas-permeable membranes that are manufactured from alternative materials, and which are resistant to fluid flow, are also workable.

Figure 2:
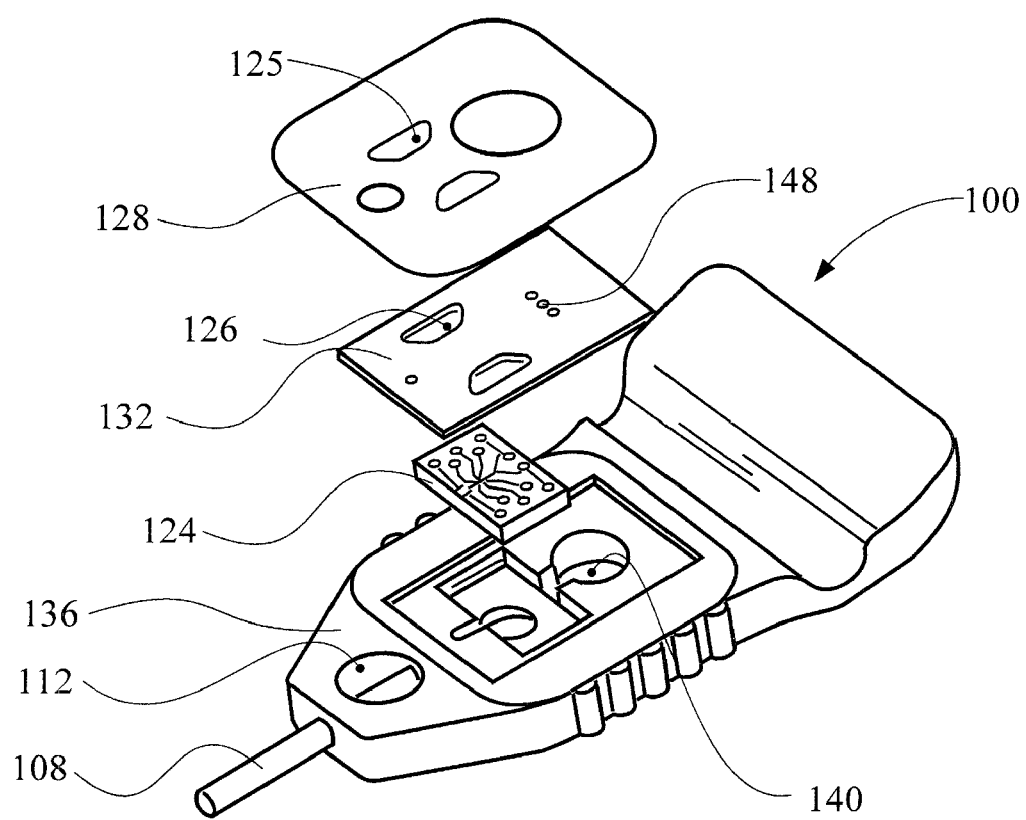
FIG. 2 is an exploded assembly view in perspective of the embodiment of FIG. 1.

A plurality of electrical contact pads, generally indicated at 120, are carried by a cartridge 100 in an arrangement adapted for coupling to an external electronic device. With reference to FIG. 2, each of the electrical contacts 120 are in electrical communication with a selected electrode disposed in an interrogation portion of a MEMS chip 124. One or more apertures 125, 126 may be included to form structure providing access to permit electrical coupling of an external device to the electrical contact pads 120.

As illustrated in FIG. 2, one embodiment of a cartridge 100 includes a tape layer 128 holding a gasket 132 in fluid sealing contact on top of a MEMS chip 120 and in reception in cartridge body 136. An operable gasket 132 may be formed from silicone sheet. A body 136 may be plastic injection molded, cast, or machined. In any case, a channel is formed through a cartridge 100 providing fluid communication between fluid receiving structure 104 and a waste chamber, such as on-board waste chamber 140. Although not currently preferred, a waste chamber may also be located external from a cartridge.

Connection structure, generally indicated at 144, may be disposed in fluid communication with the channel and arranged to couple with an external fluid motive source operable to drive fluid flow through a channel in a cartridge. Connection structure 144 may be configured as one or more illustrated orifice 148 to permit application of a pump or vacuum to urge fluid flow through a channel. It is within contemplation for connection structure 144 to include a length of conduit, or coupling structure, such as a hose barb. In certain preferred embodiments, a hydrophobic membrane barrier (not illustrated) is disposed in association with waste reservoir 140 to permit evacuation of air from a cartridge along a vent path while resisting escape of fluid from the cartridge.

It is often desirable to reduce likelihood of sample leaking from a cartridge subsequent to performing a test. For example, certain embodiments of the invention are used in analysis of blood samples, which can contain undesirable disease elements. The waste chamber 140 may include an absorbent material (such as a portion from a tissue sold under the trade name KimWipes) to participate in capillary-assisted internal flow, and/or as an aid to contain blood inside a CBC device 100 to resist spread of blood-born ailments subsequent to use of the device. Preferred embodiments may further, or also, include a hermetically sealable structure operable to contain the blood, or other fluid sample. Furthermore, closure structure may also be provided operable as a cap effective to occlude the blood collection tube 108, or fluid receiving structure 104 having another configuration.

Figure 3:
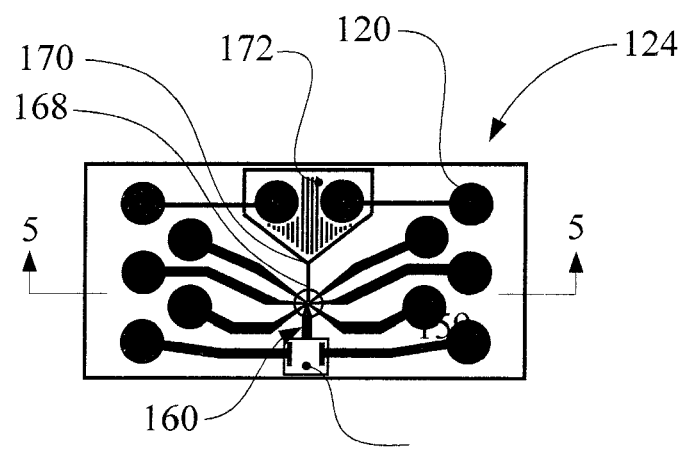
FIG. 3 is a top view of a MEMS chip component of the embodiment of FIG. 1.
Figure 4:
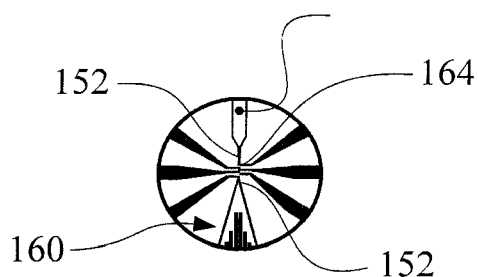
FIG. 4 is a close-up view of a portion of the MEMS chip illustrated in FIG. 3.
Figure 5:
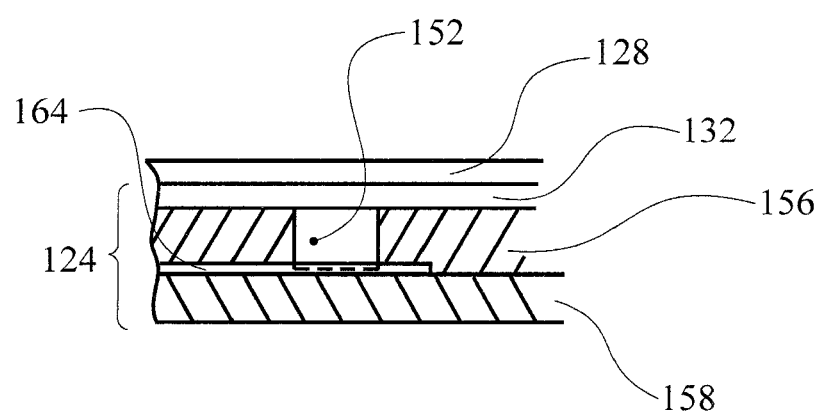
FIG. 5 is a cross-section view taken though section 5-5 in FIG. 3, and looking in the direction of the arrows.

FIGS. 3-5 illustrate additional details of construction of one embodiment of a MEMS chip 124 according to certain principles of the invention and adapted to perform a CBC test. A representative MEMS chip 124 is sized about ½ cm by about 1 cm. Certain MEMS chips 124 can be made by conventional photomasking and etching techniques. The MEMS chip 124 illustrated in FIGS. 3-5 provides a microchannel 152 that is sized to permit single-file cell passage of the red blood cells (RBC). Microchannel 152 is formed in the typically 5-20 micrometer thick epoxy photoresist layer 156. The photoresist layer 156 is typically carried on a substantially dielectric substrate layer 158.

In general, a downstream vacuum is applied to start the internal fluid/particle flow through the microchannel 152 of the illustrated MEMS chip 124. The fluid sample is urged to flow from receiving structure 104 to a receiving chamber 159 on-board chip 124. Receiving chamber may be an enlarged chamber, or simply a continuation of structure leading from fluid receiving structure 104. After passing through an optional pre-filter, generally indicated at 160, the thinned or modified whole blood flows through the microchannel 152 and over a plurality of surface electrodes 164 disposed to permit direct interrogation of the fluid sample portion that is disposed inside the microchannel 152 and between one or more pairs of electrodes 164. Fluid flow then continues along conduit portion 168, through exit 170, and into holding chamber 172. Holding chamber 172 may constitute a waste chamber 140, or may be in fluid communication with an off-chip waste chamber 140.

Certain cartridges 100 constructed according to the invention may include additional factors, such as diluents, solvents, interactors such as antigen-bound beads, or inhibitors of various kinds, which may be pre-loaded in operable position to interact with an introduced fluid/particle mix prior to interrogating that mix. Such reservoirs may be a component of a cartridge 100, or part of a chip 124. In the case of a CBC device 100, a reservoir holding diluent and/or a lysing agent desirably is arranged for mixing, typically at the start of a CBC test, with an introduced whole blood sample. The diluent may further include a blood anticoagulant (e.g. EDTA or Heparin), to resist blood clot formation in the MEMS sensor chip 124.

Figure 6:
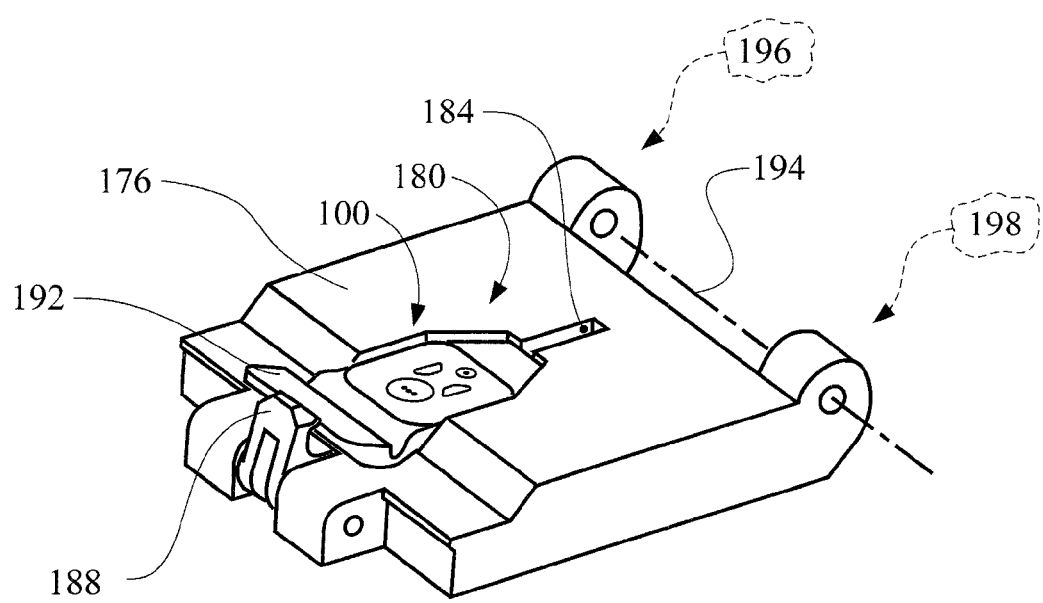
FIG. 6 is a perspective view illustrating the embodiment of FIG. 1 received in an interrogation platform.

To perform a test, such as a CBC test, using certain embodiments of the instant invention, a blood-charged CBC device 100 is placed into reception in an interrogation platform 176 (see FIG. 6). Desirably, an interrogation platform 176 includes alignment structure, generally indicated at 180, adapted to receive a cartridge 100 in an installed substantially fixed interrogation orientation and to resist installation of the cartridge in an improper orientation. One operable alignment structure 180 includes a socket 184, which may be configured to provide visual orientation clues to an operator to assist in orienting a cartridge 100. Desirably, structure is provided to maintain a cartridge 100 in a substantially fixed installed position. As illustrated in FIG. 6, biased retaining structure 188 is adapted to couple with cooperating held structure 192 of a cartridge 100 to hold the cartridge in such substantially fixed installed position.

The interrogation platform 176 carries electrode-probes (not illustrated) disposed to make physical contact with electrode contact pads 120 of the MEMS chip. One way to make such contact includes rotating a probe-carrying platen about axis 194. Contact may then be made with pads 120 by way of electrical probes having a push-pin configuration. It is within contemplation that insertion of an alternatively structured cartridge 100 can place pads 120 into reception in cooperating electrical connector structure, such as by way of an edge connector. Recall that the electrode contact pads 120 individually are in electrical communication with individual surface electrodes 164 disposed in the interrogation flow channel 152. An electrical signal may therefore be applied to pads 120 by electronic interrogation circuitry 196 associated with the interrogation platform 176 (the signal typically having a radio frequency), and impedance may be measured, across pairs of the electrodes 164.

Fluid flow of a test sample can be urged by operation of a fluid motive source 198 associated with an interrogation platform 176. Such a fluid motive source 198 may be configured to couple with connection structure 144 of the cartridge 100. Passage of cells over successive downstream pairs of electrodes during a test can be used to determine time shifting of the impedance signal between those successive pairs of electrodes 164 using a cross-correlation technique. The time of flight of the cells, used in conjunction with the cross-sectional area of microchannel 152, may be used to calculate volumetric flow rate of the blood sample. Blood-cell types can be determined based upon their unique impedance signals. Discrimination may be made between platelets, RBCs and white blood cells (WBC), as well as between types of WBCs.

Figure 7:
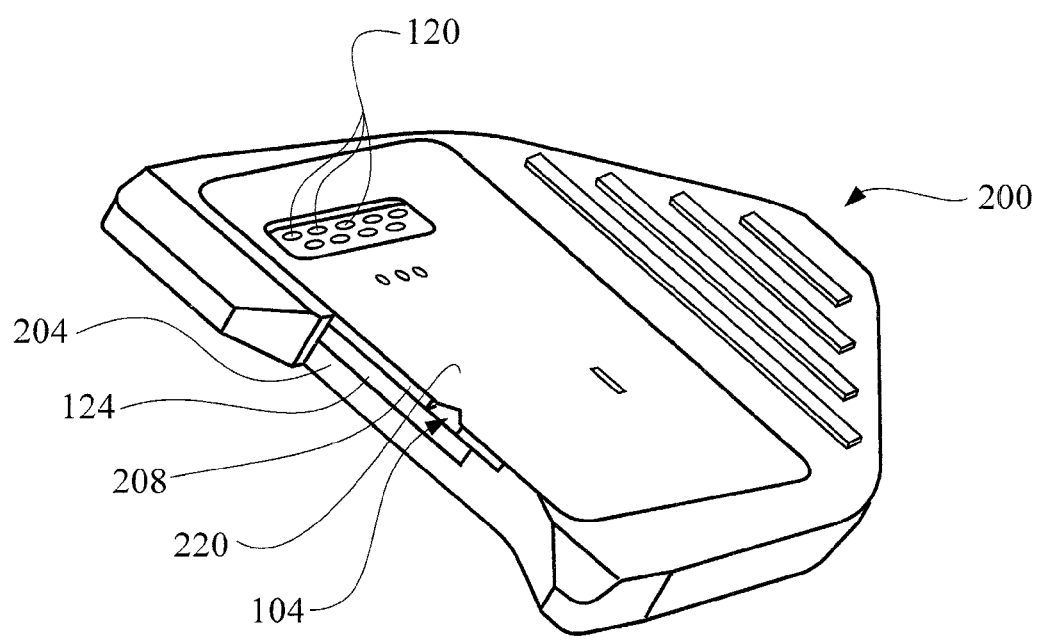
FIG. 7 is a view in perspective of a second currently preferred embodiment of a CBC device structured according to principles of the invention.
Figure 8:
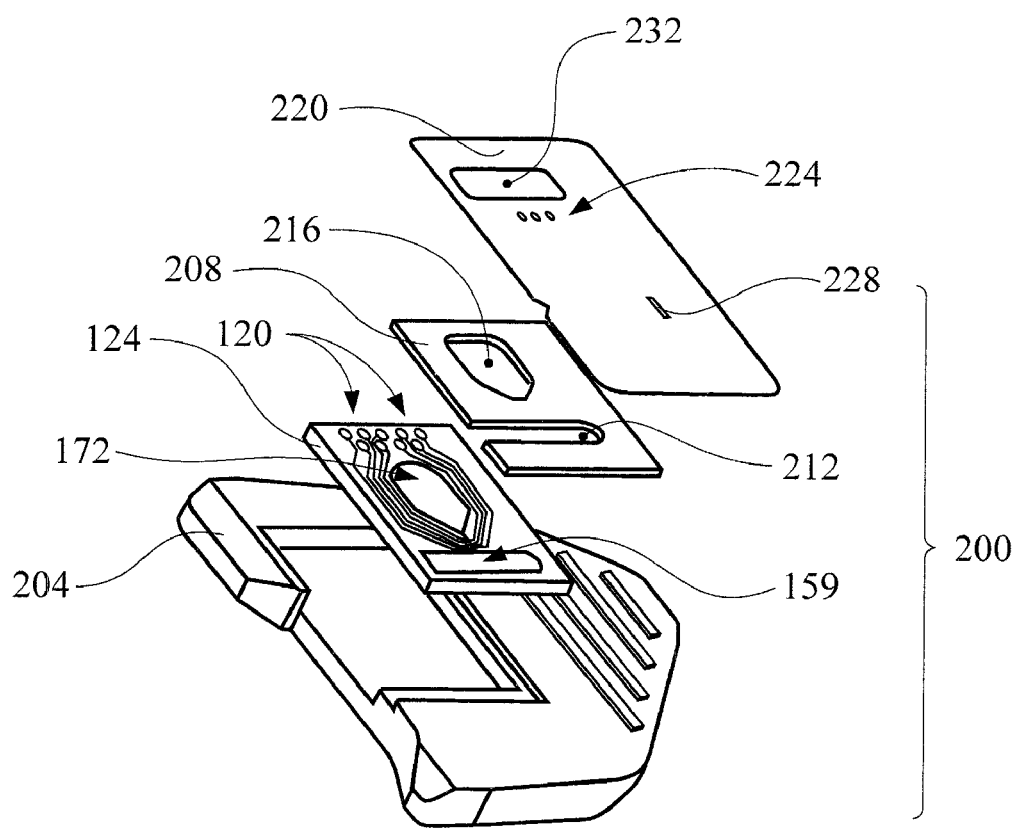
FIG. 8 is an exploded assembly view in perspective of the embodiment of FIG. 7.

An alternative embodiment of a disposable, single-use, cartridge, structured according to certain principles of the invention and generally indicated at 200, is illustrated in FIGS. 7 and 8. Cartridges 200 may be embodied to perform CBC tests, among other uses. Fluid receiving structure 104 of cartridge 200 includes a sample fluid channel entrance orifice disposed in a position effective to receive blood, or other fluid carrying particulate matter, from a fluid source for capillary, or otherwise assisted, flow into a receiving chamber 159 inside the device 200.

The illustrated embodiment 200 includes a MEMS chip 124 housed in cartridge body 204. A gasket 208 is placed on top of chip 124. As illustrated, a first vacant portion 212 of the gasket 206 forms walls for the blood channel and receiving chamber. A second vacant portion 216 of the gasket 206 forms walls for a holding chamber 172 in which to contain interrogated fluid. The gasket 208 and chip 124 are maintained in registration in body 204 by tape layer 220.

A tape layer 220 typically includes a self-adhesive surface disposed to form a sealed cover operable as a top to the chambers 159, 172 and fluid channel through the chip 200. One or more suction orifice 224 and one or more vent hole 228 are generally provided to provide communication of gases through the tape layer 220, as illustrated. The vent hole(s) 228 is/are typically occluded subsequent to charging the receiving chamber 159 with fluid. Illustrated tape layer 220 includes an open portion 132 providing access structure configured to permit electrical coupling of an external device to the plurality of electrical contact pads 120 carried by cartridge 200.

In an alternative embodiment (not illustrated) a vacuum may be applied to the MEMS chip 124 by way of a flexible diaphragm that is integrated into an alternatively structured cartridge 200. Such an alternative embodiment enhances assurance that no blood leaves the cartridge subsequent to a CBC test, and thereby decreases chance of spreading blood-born disease.

FIG. 9 illustrates another arrangement of structure desirably incorporated into a MEMS chip. The structure illustrated in FIG. 9 includes a receiving chamber 159 to hold a quantity of fluid and particulate matter, such as whole blood. A filter 160 may be provided to resist developing an undesired occlusion in a microchannel 152 by debris, or particles of too large size to pass through the microchannel 152. The electrodes 164 and corresponding contact pads 120 are illustrated in one alternative side-mounted configuration. The illustrated contact pads 120 are numbered 1-4 in series, and are in electrical communication with cooperating electrodes 164. The fluid flowing along the microchannel may be interrogated between pairs of electrodes, which generally are disposed on the "floor" of the channel.

It is typical in certain embodiments of a cartridge that the fluid mix is interrogated between successive pairs of electrodes. However, it is within contemplation for fluid to be interrogated between overlapping pairs of electrodes. For example, and still with reference to FIG. 9, one typical arrangement interrogates fluid/particles between electrodes corresponding to pads 1 and 2, and between subsequent downstream electrodes corresponding to pads 3 and 4. Alternatively, it may be beneficial in certain circumstances to interrogate fluid/particles between overlapped pairs of electrodes, such as the pairs corresponding to pads 1 and 3, and pads 2 and 4. A second alternative overlapping electrode setup includes interrogating fluid/particles flowing between electrodes 1 and 4, while also interrogating fluid/particles flowing between electrodes 2 and 3. A third interrogation scheme interrogates fluid/particles between electrodes 1 and 2, and electrodes 2 and 3.

Electrodes may be shaped and configured to provide enhanced interrogation of a particle bearing fluid. Electrodes used in certain MEMS chips 124 may be characterized as surface-mounted electrodes, which are disposed in series along a floor of an interrogation conduit, such as channel portion 152, at a plurality of axially spaced apart locations. Each surface-mounted electrode is typically disposed substantially on only one side of a cross-section through the channel 152. Such single-sided placement permits electrical communication between electrodes in a direction substantially in parallel with the axis of the channel. It is also within contemplation for surface-mounted electrodes to be configured for electrical communication across the channel. FIGS. 10B-E illustrate various electrode configurations within contemplation. Such electrodes are conveniently formed by a photomasking and etching operation. FIG. 10B illustrates twin pairs of surface-mounted electrodes, generally indicated at 232. FIG. 10C illustrates Coulter-style electrodes, generally indicated at 236. FIG. 10D illustrates a twin Coulter combination of electrodes, generally indicated at 238. FIG. 10E illustrates double-sided electrodes, generally indicated at 240, which are configured to permit electrical communication across an interrogation channel.

Figure 11:
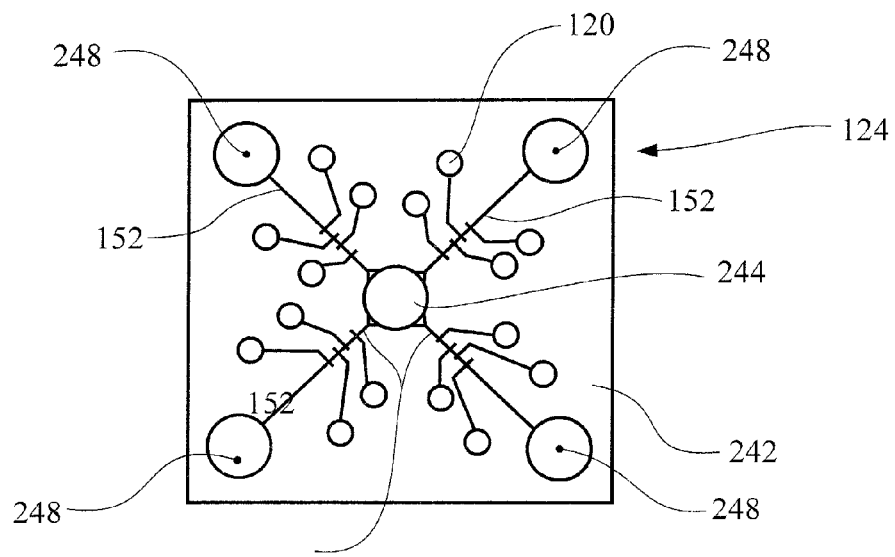
FIG. 11 is a top view of a MEMS chip structured according to principles of the invention and configured for radial dispensing of an interrogated fluid to a plurality of microchannel interrogation zones.

Devices constructed according to certain aspects of the instant invention may provide a plurality of interrogation zones on a single MEMS chip 124. For example, FIG. 11 illustrates a MEMS chip 242 adapted to provide flow in a four radial directions from an axial direction of fluid flow into a fluid entrance chamber 244. Interrogation zones are provided by sensors including electrodes located in interrogation channels 152 that permit fluid communication between chamber 244 and a plurality of holding chambers 248. Any number of interrogation zones may be provided in separate interrogation channels 152 forming spokes radiating out from a central chamber 244, within dictates of manufacturing constraints. Such plurality of hydraulically parallel sensors permit performing a plurality of simultaneous parallel electrically-based interrogations on divided subportions of a fluid sample.

Figure 12:
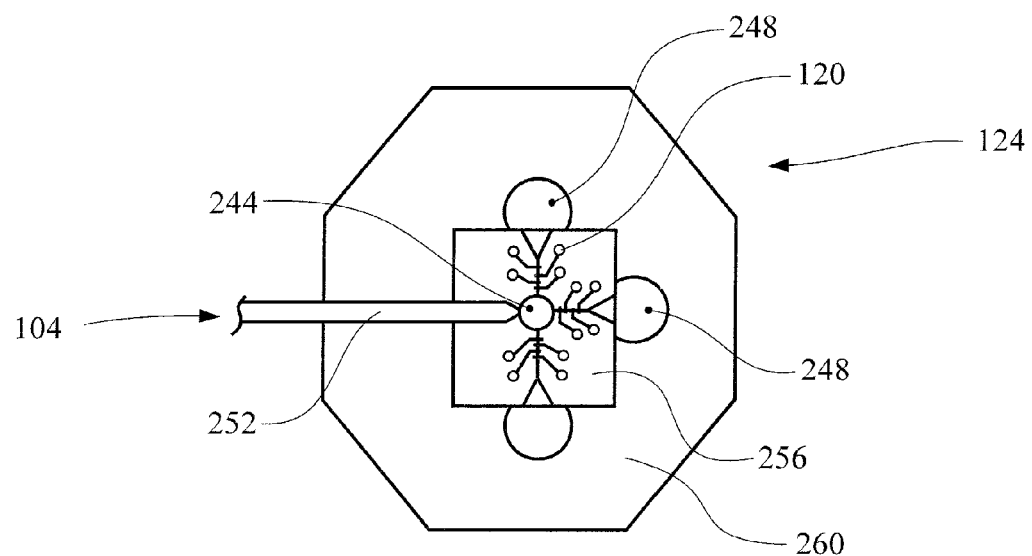
FIG. 12 is a top view of a MEMS chip structured according to principles of the invention and configured for in-plane dispensing of an interrogated fluid to a plurality of microchannel interrogation zones.

Of course, it is realized that a chip 242 may be arranged in an alternative construction to provide fluid flow into chamber 244 that is in the plane of the page. Such an in-plane fluid flow arrangement may be provided from a single supply conduit 252 and through a plurality of separate interrogation channels 152. One such in-plane fluid flow arrangement is illustrated in FIG. 12, embodied in MEMS chip 256. As illustrated by comparing FIG. 11 and FIG. 12, holding chamber 248 may be located either on-board of a MEMS chip, or on a cartridge 260. It is within contemplation to perform either parallel or serial analyses, with embodiments such as illustrated in FIGS. 11 and 12, by applying a fluid motive source, such as a vacuum, selectively to cause fluid/particle flow through an individual channel 152.

Figure 13:
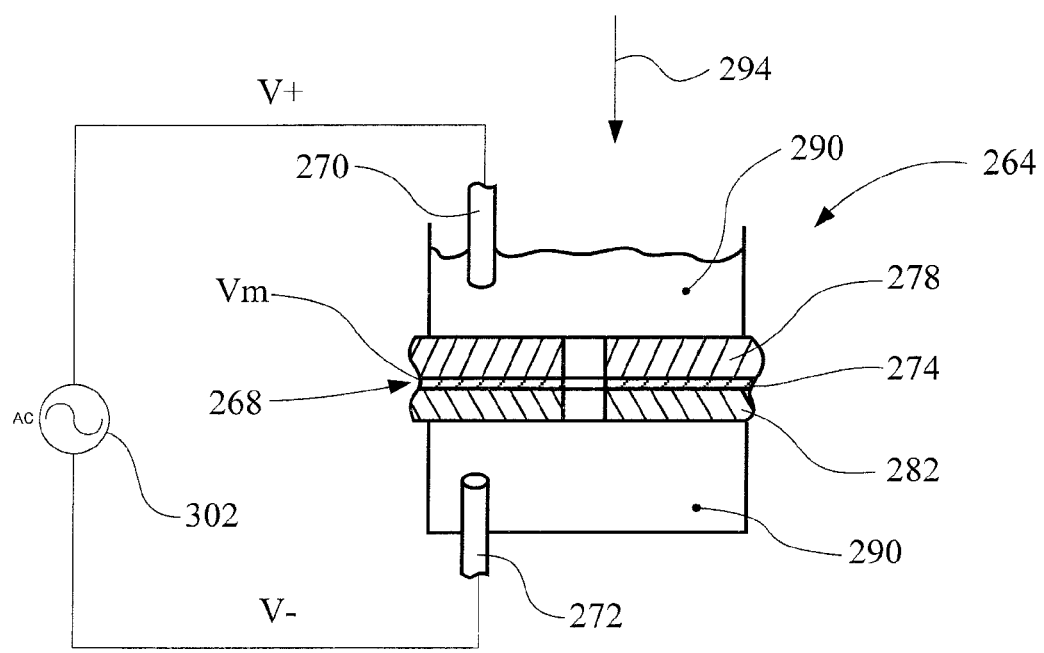
FIG. 13 is a cross-section through a first configuration of an interrogation channel of a sensor structured according to principles of the invention.

An alternative and currently preferred MEMS chip, generally indicated at 264, is illustrated in FIG. 13. Chips 264 can range in size from large to small, with a preferred chip being relatively small, at perhaps about ½ cm$^2$ in surface area. MEMS chip 264 includes a barrier element 268 disposed between a first stimulated electrode 270 and a second stimulated electrode 272. Barrier element 268 includes a detection electrode 274 sandwiched between a substantially dielectric first layer 278 and a substantially dielectric second layer 282. The dielectric material is desirably effective to resist electrical communication between each of the detection electrode 274, the first stimulated electrode 270, and the second stimulated electrode 272.

Figure 14:
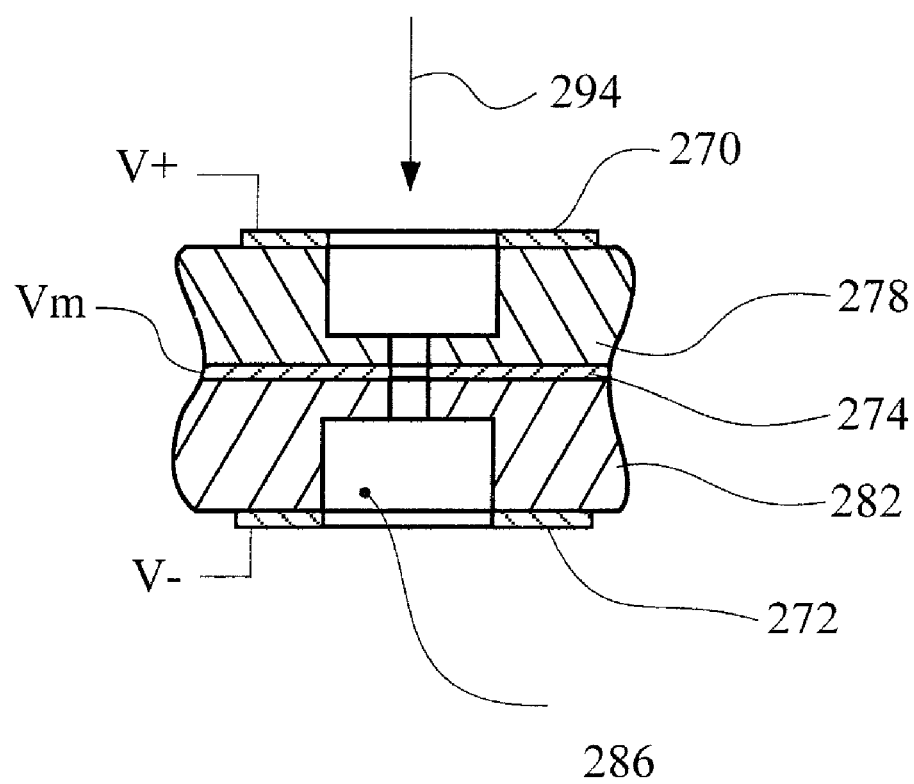
FIG. 14 is a cross-section through a second configuration of an interrogation channel structured according to principles of the invention.
Figure 15:
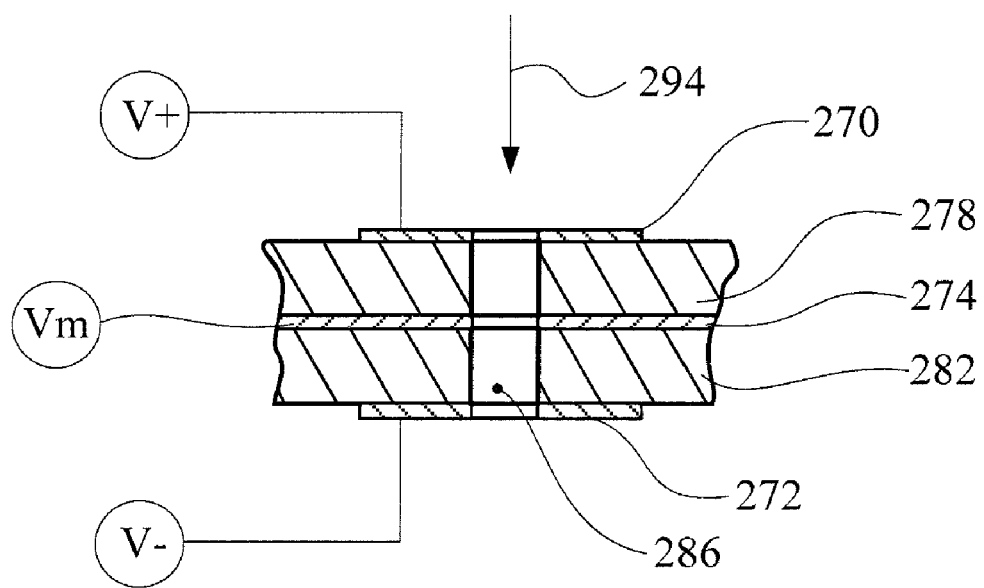
FIG. 15 is a cross-section through a fourth configuration of an interrogation channel structured according to principles of the invention.

As illustrated in any of FIGS. 13-15, the detection electrode 274 is disposed inside a Coulter style orifice formed by at least a portion of interrogation channel 286. Channel 286 form a conduit through detection electrode 274. Preferably, a fluid-contacting area of detection electrode 274 circumscribes a local portion of the conduit 286. The conduit 286 provides an electrical continuity between first stimulated electrode 270, detection electrode 274, and second stimulated electrode 272 via electrically conductive liquid 290 communicating through conduit 286. Therefore, a detection zone is formed in the vicinity of a detection electrode 274 of an electrical sensor formed inside a conduit 286. A direction of fluid flow through the MEMS chip is indicated by arrow 294.

Figure 14A:
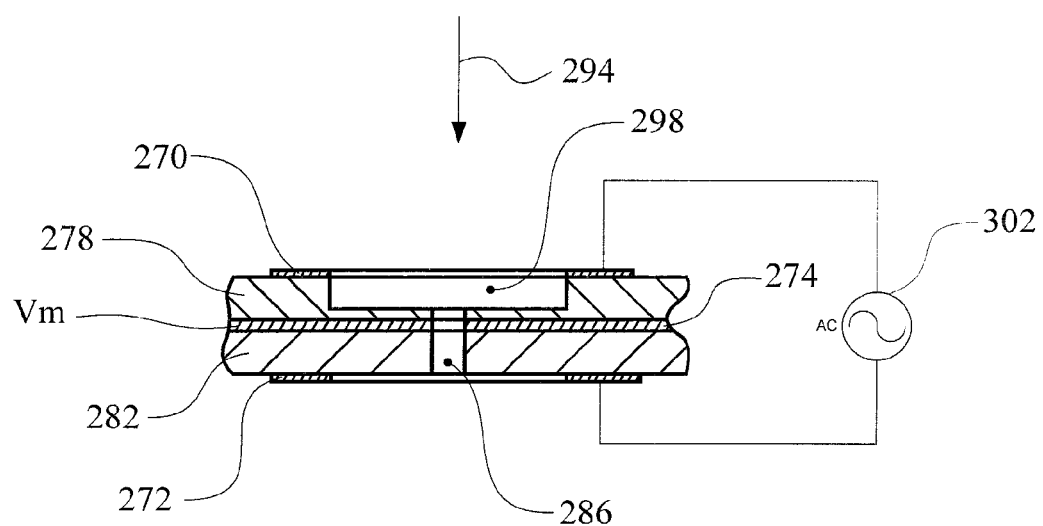
FIG. 14A is a cross-section through a third sensor, similar to that illustrated in FIG. 4, but having asymmetrical construction.

The interrogation channel 286 typically has an approximately circular cross-section for simplicity of manufacture. Alternative configurations are also workable, including rectangular and oval, among others. A channel 286 can be manufactured by micromachining methods, including laser drilling, water drilling, plasma etching, and the like. The currently preferred "small" sizes for a chip 264 encompass channels 286 having diameters between about 3-150 microns. Larger devices constructed according to principles of the invention may simply be drilled with conventional mechanical machining methods, including drilling, or with water jet or laser cutting. In devices adapted to perform a CBC test, the diameter of an interrogation channel may be around 10 micrometers. In a device adapted to perform a CD4+ test, the channel may have a diameter of about 35 micrometers. FIGS. 14, 14A, and 15 illustrate operational variations on configuration for channels 286, including variations in length, opening size, and relative closeness between the interrogation electrode 274 and excited electrodes 270 and 272. A channel 286 may be constructed to have an entrance 298 that forms a metering structure, or may include a restriction within the channel 286, such as illustrated in FIG. 14.

It is within contemplation to provide surface coatings to reduce impact from contact with the sensor structure and the fluid passing therethrough. Desirably, suitable coatings are applied to surfaces of a chip or cartridge that contact sample fluids. Such coating arrangement can be provided to reduce the clotting cascade in whole blood samples, for example. Coatings operable in sensors for use with such blood samples include Teflon, heparin, and PRO-based materials.

Each insulating layer 278, 282 may be formed from any material resistant to conductance of electricity. The insulating layer simply must function to place electrodes in electric isolation from each other, except for communication along (typically) a proscribed fluid path. However, it is currently preferred for the insulators to be formed from flexible, film-like plastic materials, including polyamides and polyesters such as Mylar and Kapton, respectively. Such films may be on the order of 0.0001 to 0.010 inches (2-200 microns) in thickness, although thinner or thicker materials may be used, as desired for particular applications. Chips or sensors 264 with resisting layers 278, 282 made from thin film materials are sometimes characterized as flexible chips. The instant invention can be embodied using virtually any thicknesses for substrate insulators and electrodes, However, thickness of insulator and electrode layers, and channel sizes, in a particular sensor are typically sized in accordance with the intended use of that particular sensor. As non-limiting examples, it is within contemplation to form an alternative insulator layer from nonconductive sheet or plate material, or even from a portion of an electronic circuit board.

Electrodes are generally made from metal or alloys of metals, including Aluminum, Platinum, Gold, Copper, Silver, Chromium, Iridium, Titanium, and the like, although any other operable electrically conductive material would suffice. It is currently preferred to coat the interrogation electrode (and sometimes one or more of the excited electrodes), onto an insulator film to improve material handing characteristics during assembly of the sensor. The coating operation may be carried out by electroplating, electro-chemical deposition, or using some other known method, such as sputtering or electro-deposition techniques, and the like. It is further within contemplation to incorporate micro-machining methods, such as masking and etching, as well as screen printing techniques and laser etching, to formulate individual electrode structures.

In one use of a chip 264, a voltage induced by a signal generator 302 is applied to stimulate each of electrodes 270 and 272. Typically, the applied voltage, or electric signal, is a fluctuating voltage, typically having opposite sign ($V^+$ and $V^-$) and the same magnitude at each stimulated electrode. A passive voltage $V_m$ corresponding to the imposed signal, and any effect due to presence of one or more particles, is measured at the interrogation electrode 274 disposed between the stimulated electrodes 270 and 272. The measured signal from chip 264 changes sign, and thereby causes a more distinct measured signal when compared to a signal generated in chips embodied as illustrated in FIG. 3. The arrangement illustrated in FIG. 13 dramatically improves signal-to-noise ratio. Furthermore, the effect on the magnitude of measured voltage at the detection electrode due to particle departure from a consistent path is significantly reduced.

Details of construction of a currently preferred flexible MEMS chip, generally indicated at 310, will now be made with reference to FIGS. 16-18. It is currently preferred to provide alignment features, such as the illustrated holes 314, to assist in alignment of the constituent structures as respective layers forming the device are "stacked" on one another. The stacked components form a sensor assembly 310 that may be regarded as a "chip".

A plurality of interrogation channels 286 may be provided, numbering from one to as many as desired, up to a limit perhaps imposed by manufacturing or data acquisition considerations. The device illustrated in FIGS. 16-18 has eight interrogation channels 286 that may be used to perform a simultaneous parallel analysis of the fluid flowing therethrough. It is currently contemplated to manufacture sensor devices with up to 200, or more, parallel channels. In any case, it is currently preferred to form the channel 286 to provide a continuous stretch of electrode material disposed as a ring section of the channel. Such an encircling electrode configuration tends to average out the signal produced in the measurement electrode 274, substantially regardless of the relative position of an undersize particle with respect to the channel centerline.

Figure 16:
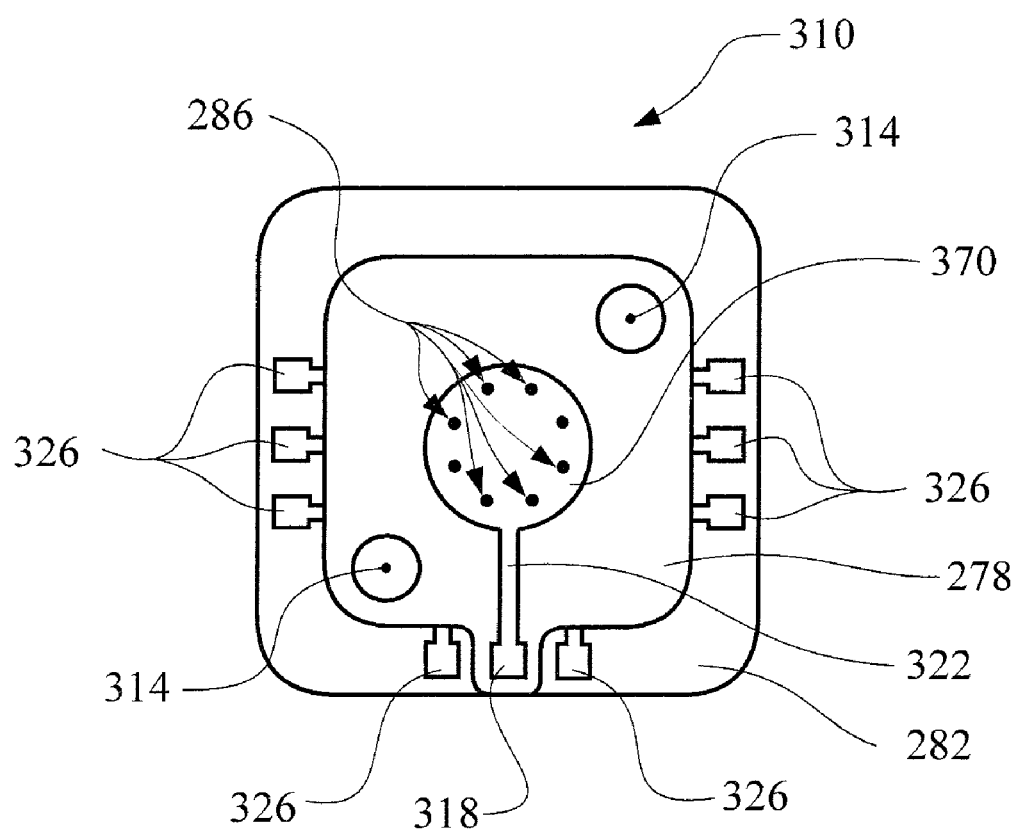
FIG. 16 is a top view of a sensor structured according to principles of the invention.

With reference to FIG. 16, each channel 286 is arranged to pass through the stimulated electrode 270. A contact pad 318 is configured to communicate an electric signal from an external device along electric trace element 322 to the electrode 272. The electrode 270, electric trace element 322, and contact pad 318 may be patterned on one side of dielectric layer 278. Electrode 270 forms a plurality of electrodes, one associated with each channel 286, that are electrically in common.

Figure 17:
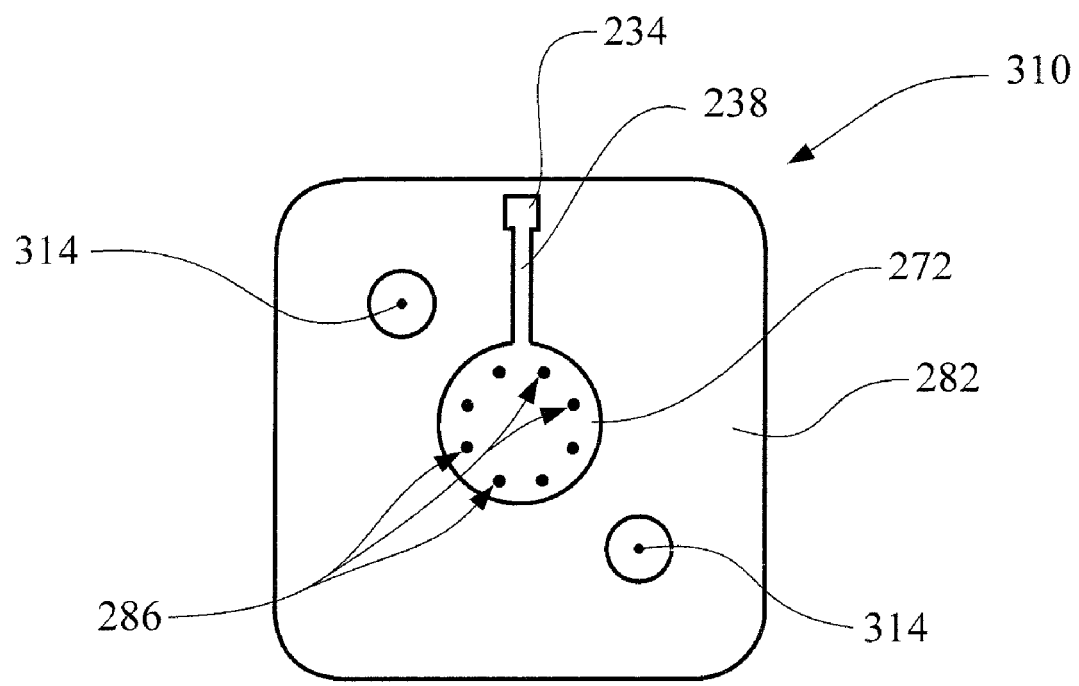
FIG. 17 is a bottom view of the sensor of FIG. 6.
Figure 18:
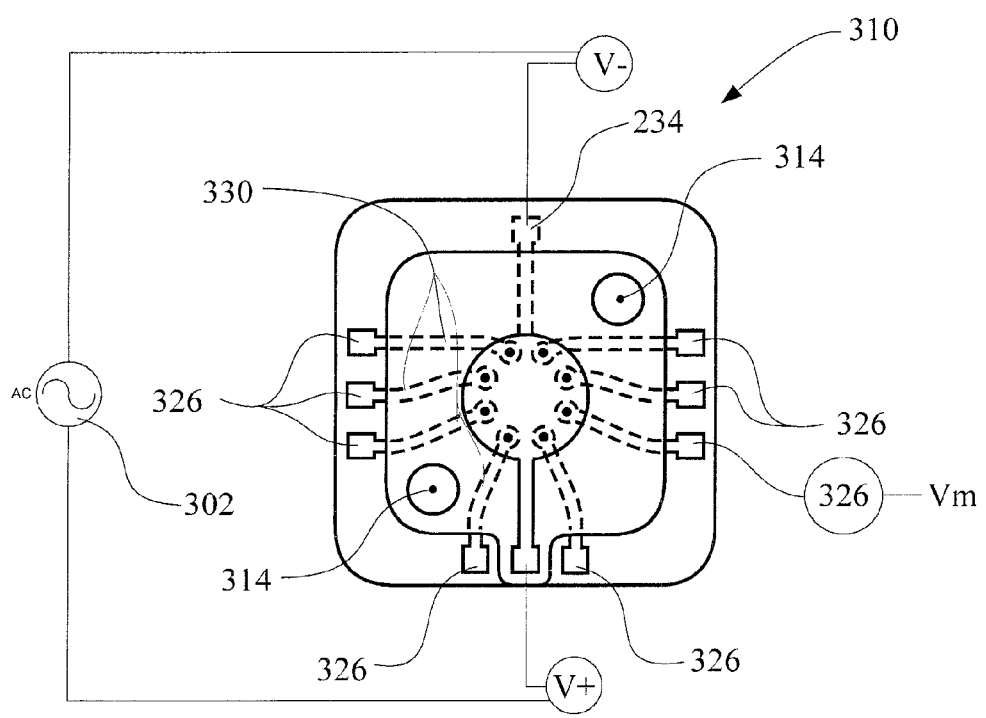
FIG. 18 is a top view of the sensor of FIG. 6, with certain components shown in partial transparency to reveal a currently preferred internal structural arrangement that forms an 8-channel sensor.

With reference to FIG. 18, one or more detecting electrode 274 can be patterned on the opposite side of layer 278, and arranged to encompass a desired area in vertically stacked relation to the electrode 270. As illustrated, eight such electrodes 274 are provided in the embodiment of FIGS. 16-18. Each illustrated electrode 272 includes a contact pad 326 that communicates electrically with the electrode through electric trace element 330. Note that a stretch of a channel 286 passes through a respective detecting electrode 272.

With reference to FIG. 17, the bottom side of the sensor 310 carries stimulated electrode 272 and contact pad 334 for connection of the electrode to external signal generator, such as signal generator 302. Contact pad 334 communicates an electric signal from a signal generator to the electrode 272 by way of an electric trace element 338. In general, electrode 272, trace element 238, and contact pad 334 are patterned on insulating layer 282 prior to assembly of the layers to form a chip 310. Note that channels 286 continue through the stimulated electrode 272. Electrode 272 forms a plurality of electrodes, one associated with each channel 286, that are electrically in common.

Sensors formed in certain chip embodiments are desirably configured to provide spacing between electrodes with the spacing being on the order of the size of a characteristic size, such as a "diameter" of a particle of interest. If the spacing is even smaller, such as one-half the characteristic dimension, the resolution of the sensor portion may be even better. For a CBC or CD4 device, it is currently preferred to manufacture a substrate layer from Kapton, due to the high melting temperature (350° C.) inherent in Kapton. The electrodes may conveniently be patterned on such substrate, and a second insulating layer of Mylar can be heat bonded to the substrate layer. Due to the thicknesses of the thinnest commercially available sheet of each material, the Kapton layer is typically about twice the thickness of the Mylar layer in currently preferred embodiments of the invention. Such difference in thickness of insulating layers can result in a bias, or a signal offset from zero in the absence of a particle, in a signal measured at a detecting electrode 274 sandwiched between the layers. Such bias can be reduced or eliminated by forming a larger entrance or exit, such as entrance 298 in FIG. 14, in the thicker insulating layer. An optimized such entrance can be configured to provide a substantially electrically equivalent resistance between each stimulated electrode and a detecting electrode sandwiched therebetween.

While a single interrogation "layer" is illustrated in FIGS. 13-18, it is within contemplation to form alternative MEMS chips having a plurality of stacked interrogation layers, to provide a plurality of interrogation electrodes arranged along an axis of the interrogation channel 286. Such alternative chips would enable serial analysis of a sample along a single conduit 286. Furthermore, certain alternative serially stacked chips including a plurality of channels 286 would be capable of simultaneous parallel and serial analysis of a fluid sample.

Figure 19:
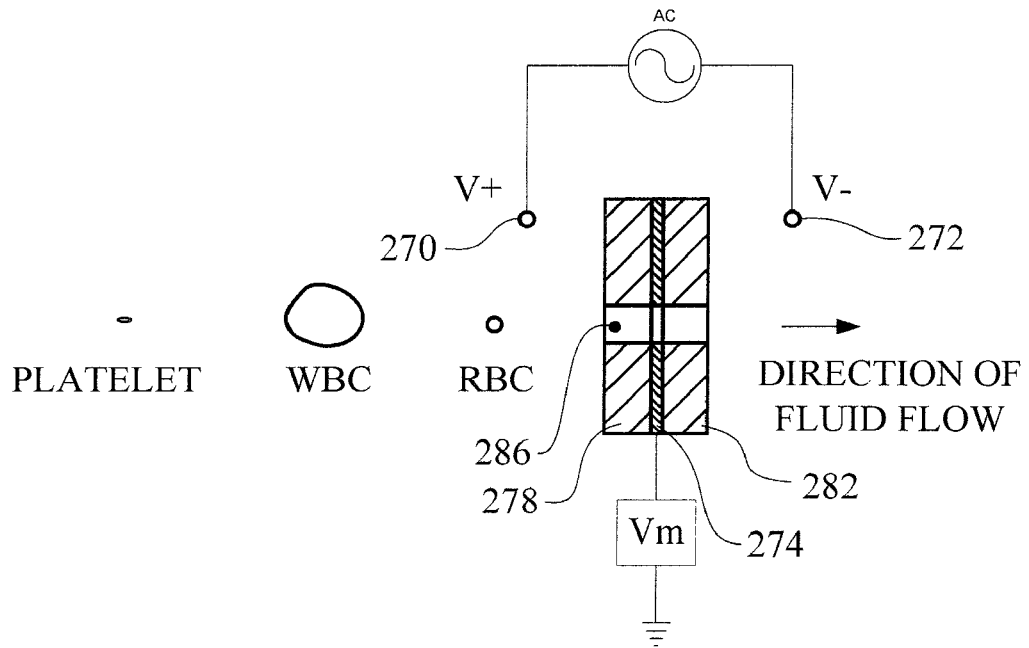
FIG. 19 is a cross-section view through an interrogation zone structured according to principles of the invention, and showing three particles lined up for successive passage through the zone.
Figure 20:
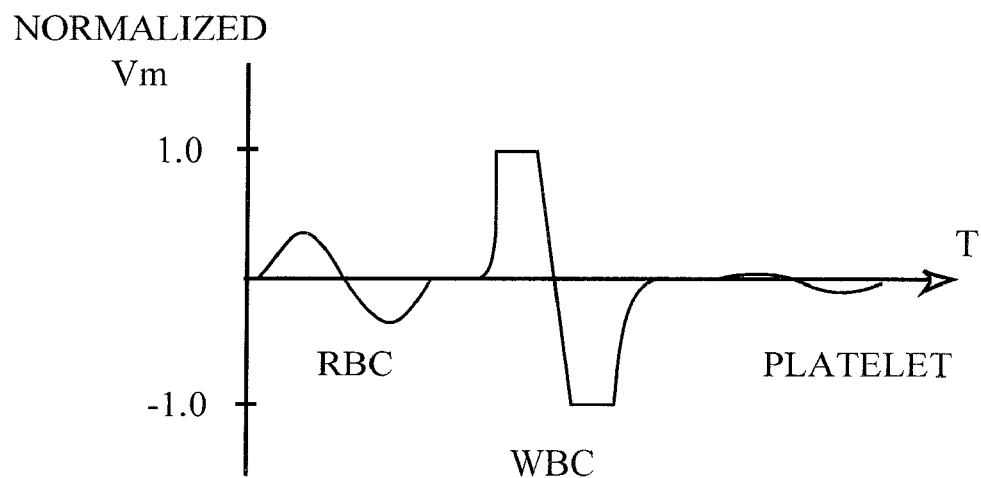
FIG. 20 is a plot representing measured values of passive voltage induced by the particles and interrogation zone illustrated in FIG. 9.

FIGS. 19 and 20 illustrate an experimental set up structured according to principles of the invention, and data corresponding to the illustrated arrangement, respectively. FIG. 19 depicts three particles; blood cells of different types, prepared to travel in succession through an interrogation channel 268 embodied in a thin film chip structured according to principles of the instant invention, such as chip 310. For use with fluids having particles sized in accordance with particles in whole blood, the illustrated channel 286 is desirably about 10 micrometers in diameter, and can be between about 4 to about 400 micrometers, or so, in length. In such devices, the channel diameter can range between about 3 to about 150 micrometers, or so. The data shown in FIG. 20 assume an approximately constant and uniform travel velocity of the particles through the channel. The red blood cell (RBC) is smaller than the channel diameter, but produces a distinctive signal. The white blood cell (WBC) is larger than the channel, but can extrude therethrough. Contact between the WBC and the interrogation electrode produces a maximum signal, essentially "railing" the device. The platelet, being of much smaller size, causes a lesser, albeit a distinct and discernable, signal.

FIGS. 21A and 21B illustrate one exemplary arrangement forming a single-use cartridge constructed according to certain principles of the invention, and generally indicated at 350. The cartridge 350 may include a snap-on cap 354, as illustrated, to resist escape of a portion of a loaded fluid sample through the sample collection structure 104. Snap-on cap 354 may maintain sterility before and after loading the sample. A cap 354 may also contain one or more fluids for use during a test, such as a diluent, solvent, or inhibitors of various kinds, that may be pre-loaded in operable position to interact with an introduced fluid/particle mix prior to interrogating that mix. A representative cartridge 350 may be between about 1 and 3 inches in a longest direction, although longer and shorter cartridges are operable. The body 358 of cartridge 350 is configured to provide a measure of protection to contact pads 120, and to couple them in electrical communication with an interrogation platform, such as platform 176.

Figure 23:
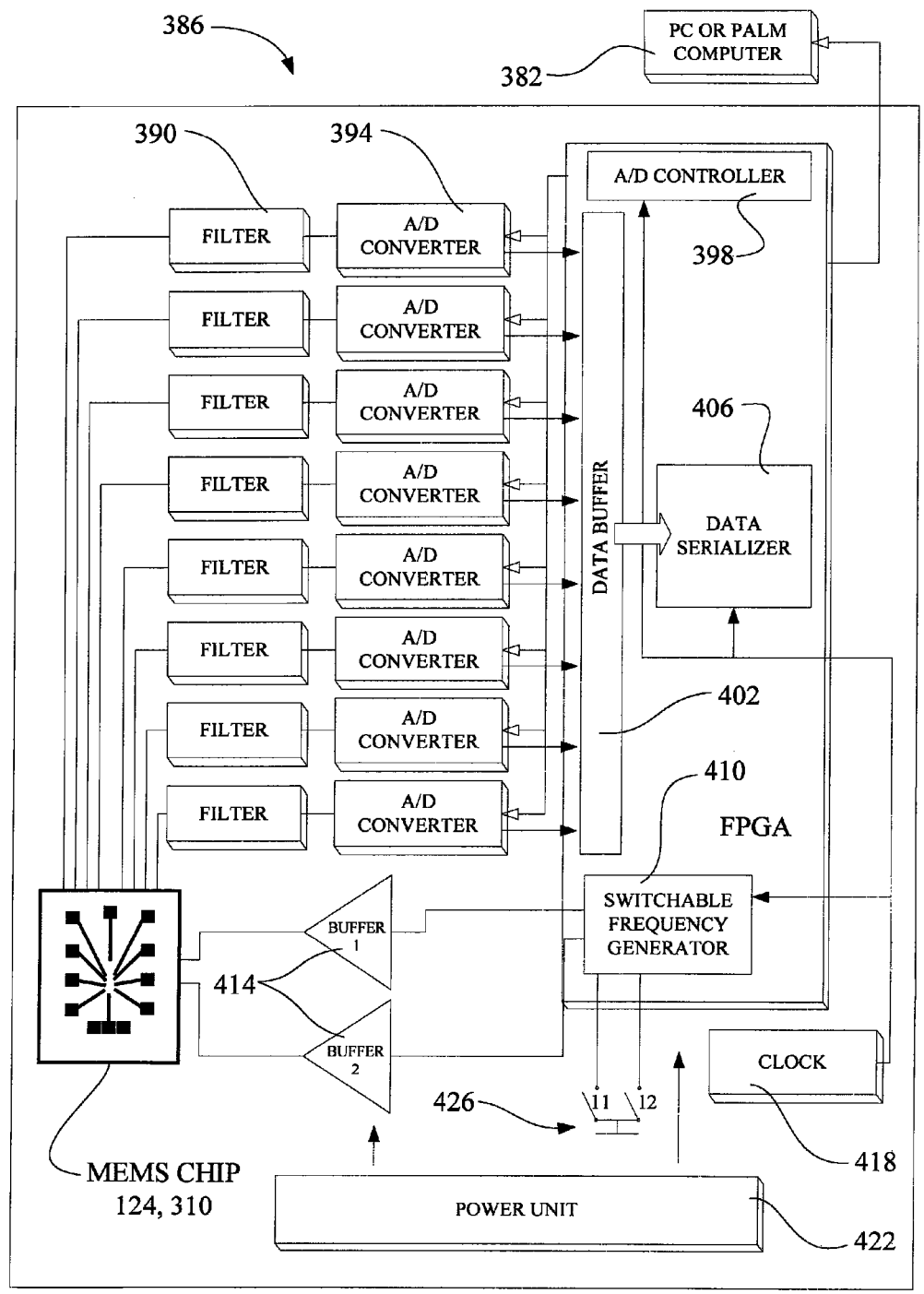
FIG. 23 is a schematic illustrating currently preferred electronic interrogation circuitry adapted to interface with a sensor structured according to principles of the invention.

FIGS. 22 and 23 illustrate operable embodiments of electronic interrogation circuitry 196 that may be associated with an interrogation platform 176. Such circuitry may include a multiplexor 362 to cycle signals and/or measurements between a plurality of electrodes. A signal generator 302 is adapted to output a desired signal to a plurality of contact pads on the MEMS chip being interrogated. An A/D converter 366 typically modifies the collected analog detection signal for use by another device. Representative such devices include a computer platform 382, such as a PDA, hand-held computer, and a desktop or laptop computer. Electronic elements including one or more band pass filter 370, amplitude detector 374, and phase detector 378 may be included in an operable electronic arrangement 196.

FIG. 23 illustrates a currently preferred arrangement for electronics 386 that may be included in circuitry 196. Electronic arrangement 386 includes a plurality of filters 390 and A/D converters 394 adapted to interface with an A/D controller 398. A signal received from a detecting electrode is routed through a filter 390 and A/D converter 394 to a buffer 402 and data serializer 406 for output as a signal modified for use by a computer platform 382. A signal from a switchable signal generator 410 may be selectively applied through buffers 414 to a plurality of stimulated electrodes, such as 270 and 272 in FIG. 13. A clock 418 may be used to drive the signal generator 410. A power supply 422 may provide power to the components through a switch, generally indicated at 426.

Figure 24:
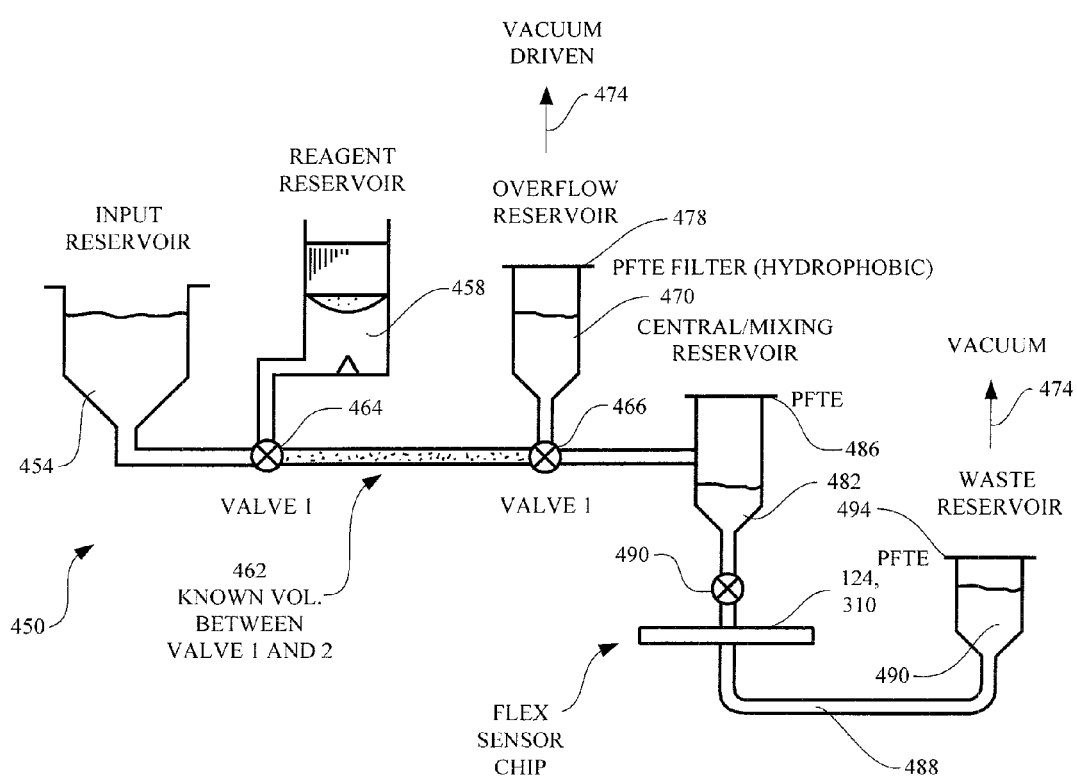
FIG. 24 is a schematic illustrating structure associated with a currently preferred embodiment of the invention.

FIG. 24 illustrates structure, generally indicated at 450, that desirably is provided on certain cartridges according to certain aspects of the invention. The input reservoir may be a chamber, or a portion of the channel from receiving structure 104 flowing through a cartridge. A reagent reservoir 458 may be disposed in a cap 354, or on-board a cartridge. In any case, if present, a reagent reservoir 458 is generally placed into fluid communication with the sample for mixing prior to interrogation in a sensor portion of the cartridge.

It is sometimes desirable to provide a chamber 462 defining a known volume in which to select a portion of the introduced fluid sample for evaluation in the sensor portion of the cartridge. Such chamber 462 may conveniently be defined between a first valve 464 and second valve 466. In the arrangement 450, the chamber 462 may be sequentially used to measure a quantity of sample fluid, and a quantity of reagent. Fluids may be drawn into an overflow chamber 470 by a vacuum 474, or other motive source operable to urge fluid motion. The overflow chamber can operate to verify, or to ensure, that complete filling of the chamber 462 occurs. A hydrophobic membrane 478 is typically positioned to permit gasses to exit the cartridge, but to resist escape of fluids from the chamber 470.

In general, a hydrophobic membrane, such as membrane 478, may be formed from a thin sheet of Teflon, or Teflon-like material. Certain Teflon-based materials are also operable. It is within contemplation to form a membrane from Teflon coated or impregnated materials. Certain other materials, such as polystyrene, may be formed into an alternative workable gas permeable and fluid retaining membrane.

A central mixing chamber 482 may be included on a cartridge to permit mixing of a reagent with the introduced fluid sample to form a modified test fluid. Fluid can be drawn into mixing chamber 482 by a selective suction of gasses through a hydrophobic membrane 486. A valve 490 may be included on a cartridge as a fluid-flow control device. Subsequent to test sample preparation, such valve 490 may be opened and fluid may be urged to flow through one or more sensors of a MEMS chip, such as chip 124 or 310. In most cases, test fluids are urged to flow from a MEMS chip along a channel 488 into a waste chamber 490 contained in the cartridge. Again, a venting membrane 494 desirably is provided in association with the chamber 490 to permit gasses to exit the cartridge while resisting escape of fluids. Membrane 494, in combination with a fluid motive source and one or more valves 464, 466 and 490 serves as a way to facilitate control of fluid flow through a cartridge.

Figure 25:
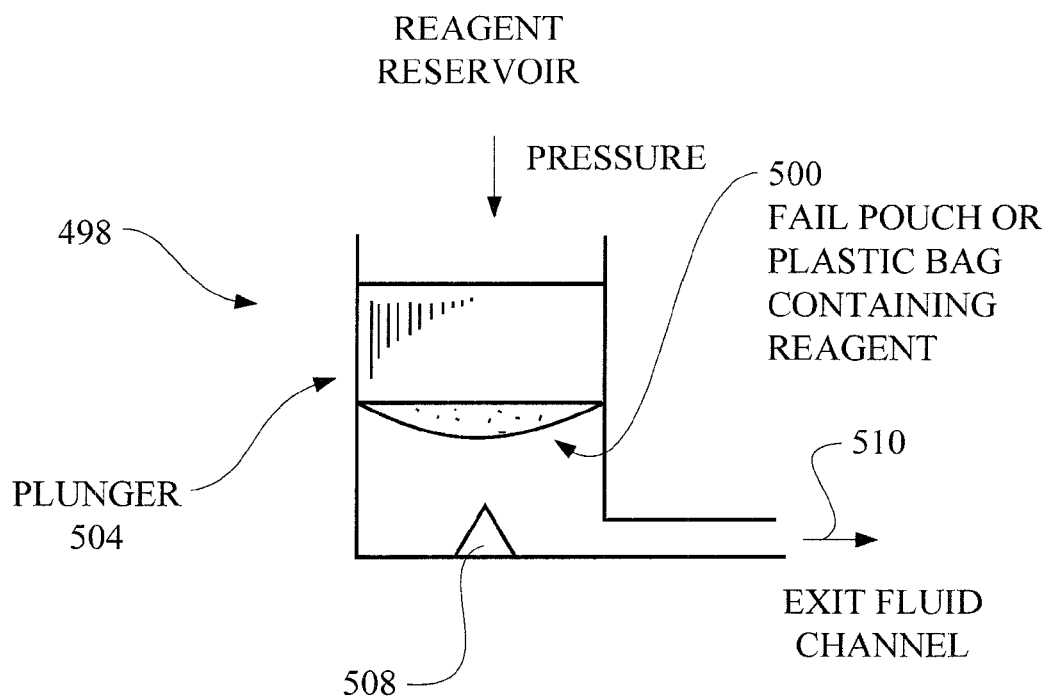
FIG. 25 is a side view of a reagent-holding fluid distribution arrangement operable in certain embodiments of the invention.
Figure 26:
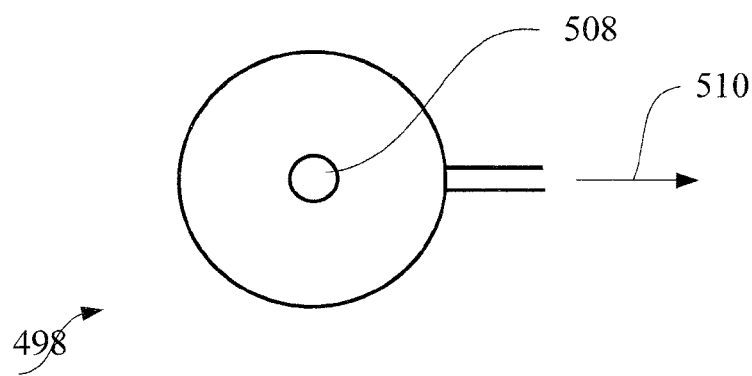
FIG. 26 is a top view of the embodiment illustrated in FIG. 25.
Figures 34, 35, 36:
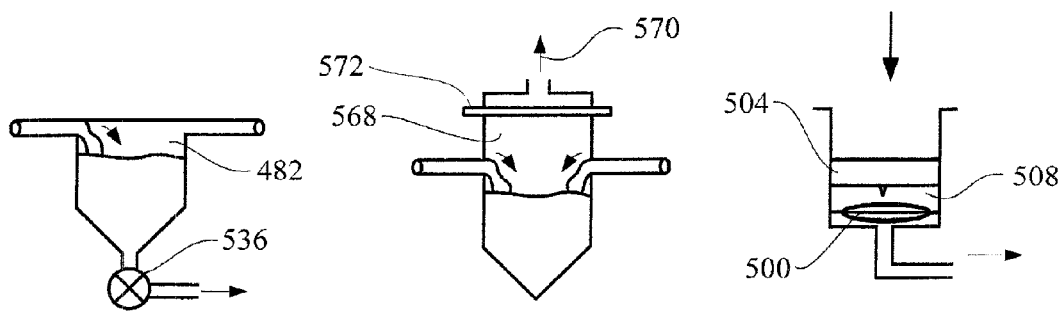
FIG. 34 is a side cross-section view of the mixing chamber in FIG. 33.
FIG. 35 is a side cross-section view of a chamber in FIG. 33.
FIG. 36 is a side cross-section view of an operable sample chamber portion of a cartridge, including a rupturable container.

As illustrated in FIG. 25, certain embodiments of a cartridge include dispensing structure, generally indicated at 498, for a reagent that is confined in packaging, such as a pouch or packet 500. The pouch can be made from foil, plastic, or other material effective to form a rupturable membrane in which a fluid may be temporarily confined. A convenient way to dispense the reagent from a packet 500 is also illustrated in FIGS. 25 and 26, where a plunger 504 is adapted to press packet 500 into engagement with rupturing structure 508. Certain operable rupturing structure 508 can be embodied as a needle-like pointed object, or may provide a sharp edge, such as a knife edge, or a jagged edge. The plunger 504 may also be employed to urge flow of the reagent through a cartridge as illustrated by arrow 510, e.g. to mix with a sample in the cartridge. It is also within contemplation for piercing structure 508 to be associated with a plunger 504, such as illustrated in FIG. 36.

Figure 27:
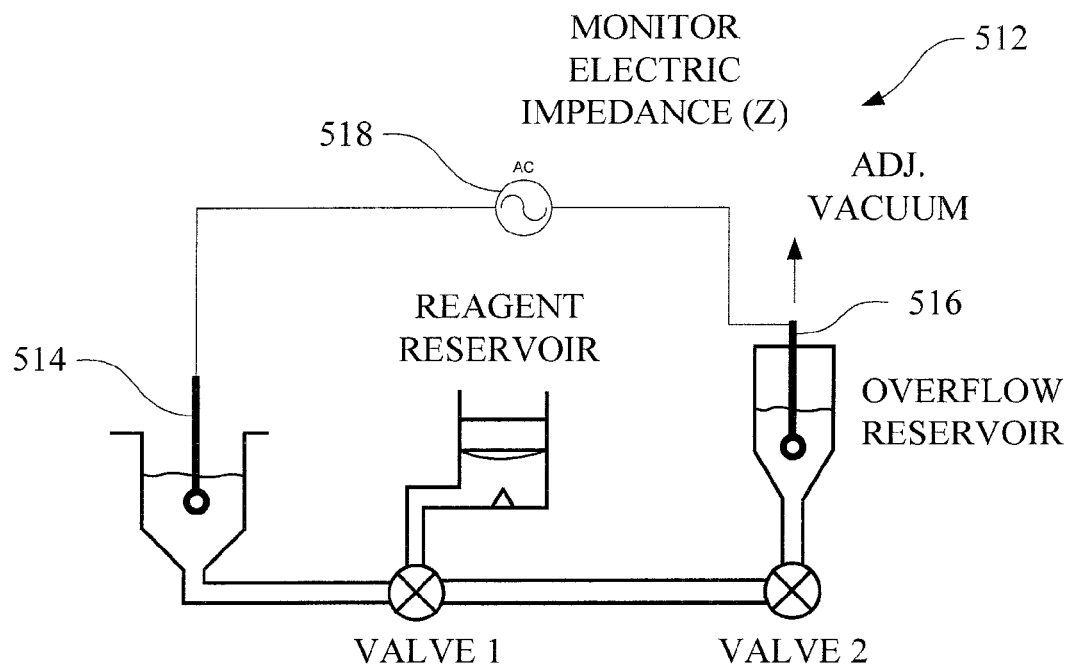
FIG. 27 is a schematic illustrating structure associated with a currently preferred embodiment of the invention adapted to ensure presence of a bubble-free fluid sample.
Figure 28:
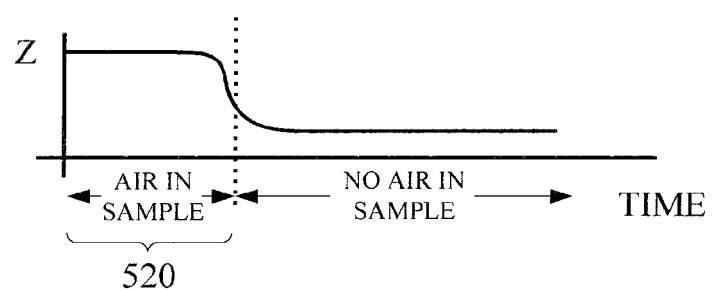
FIG. 28 is a plot of impedance representative of measured values during a test performed with the embodiment of FIG. 27.

Sometimes, a cartridge may include bubble detection structure. One workable bubble detection structure is indicated generally at 512 in FIG. 27. An electrode 514 is disposed upstream of an area to be monitored for presence of bubbles. A second electrode 516 is disposed downstream of the monitored area. An impedance monitor 518 is applied in-circuit between the electrodes 514, 516 to monitor impedance between them. The graph illustrated in FIG. 28 represents data that might be collected during operation of the bubble monitor 512. During time period 520, presence of one or more bubbles causes high impedance. Once the air or gasses are removed or replaced with gas-free solution, a discernibly lower impedance is measured.

Figure 29:
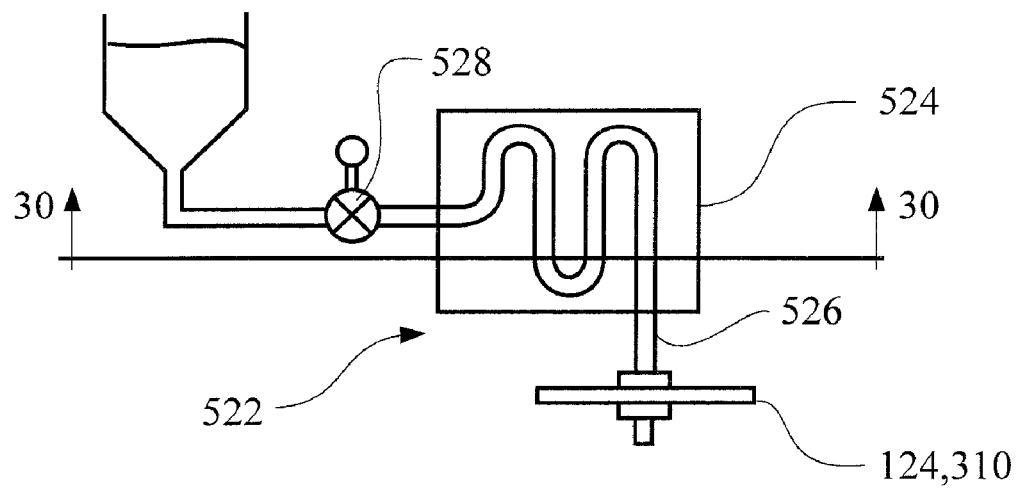
FIG. 29 illustrates structure of an air bubble remover that may be included in certain embodiments of the invention.
Figure 30:
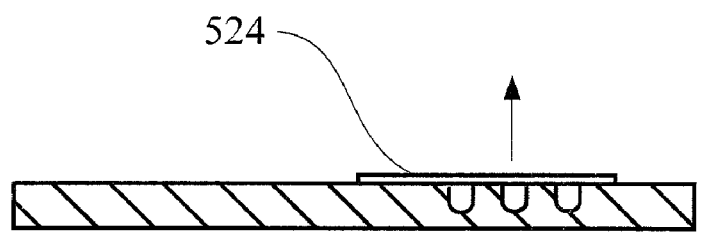
FIG. 30 is a cross-section view taken through section 30-30 in FIG. 29.

A bubble removing structure, generally indicated at 522 in FIGS. 29 and 30, desirably is included in certain cartridges to ensure no bubbles are present in a sample prior to conducting a test. An operable bubble removing structure 522 may be formed by associating a hydrophobic membrane 524 with a chamber or portion of a channel 526. A vacuum applied to one side of the membrane is therefore effective to remove gasses from the fluid retained on an opposite side of the membrane 524. In a preferred embodiment, the bubble remover 522 is associated with a chamber having a known volume, effective to produce a bubble-free known volume of fluid for testing by a MEMS chip 124, 310. In such preferred embodiments, a particle count-per-known-volume may be obtained. Once the known volume is obtained, a vent or valve 528 may be opened to permit urging the test sample fluid through the MEMS chip 124, 310 for interrogation in a sensor portion of the chip.

Figure 31:
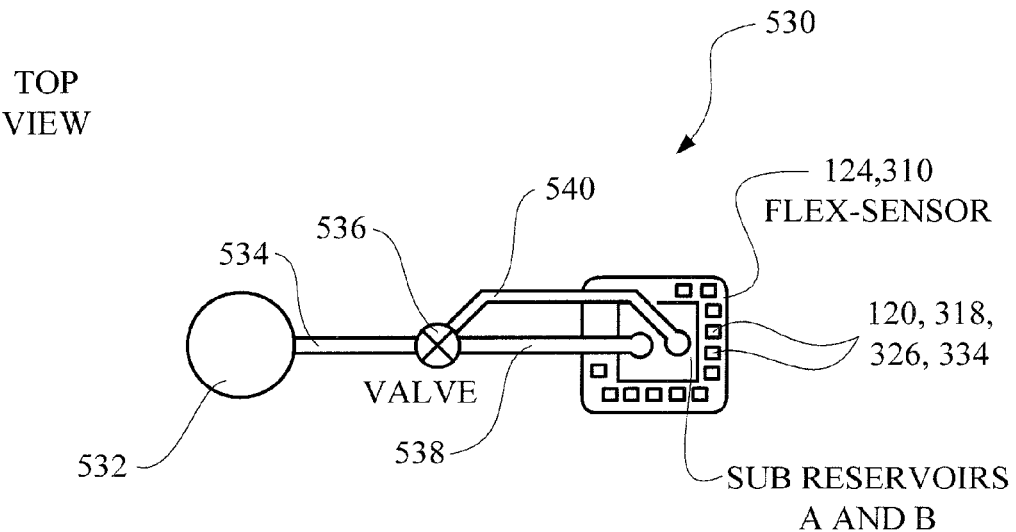
FIG. 31 is a top view of a portion of structure carried by a cartridge structured according to certain aspects of the instant invention and adapted for serial and/or parallel interrogation of a fluid sample through a plurality of differently structured interrogation channels.
Figure 32:
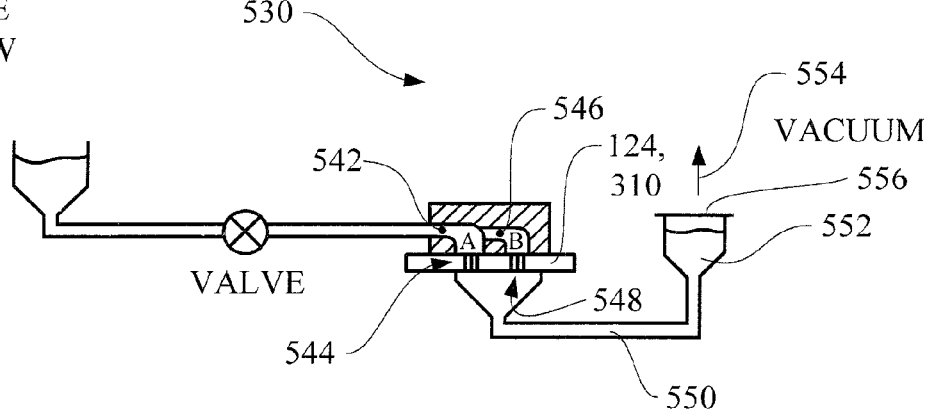
FIG. 32 is a side cross-section view of the structure illustrated in FIG. 31.

Sometimes, a cartridge may carry structure arranged to deliver portions of a sample through selected channels to different sensors of a MEMS chip. One such arrangement is indicated generally at 530 in FIGS. 31 and 32. Fluid from a chamber 532 flows through a channel portion 534 to valve 536. Valve 536 may be oriented to permit flow through either of channel portion 538 or channel section 540. Channel portion 538 terminates at entrance area 542 near sensor portion 544 of the MEMS chip 124, 310. Channel portion 540 terminates at area 546 near sensor portion 546 of the MEMS chip 124, 310. The sensors 544 and 546 may be similar to each other, or may be differently structured to interrogate different populations of particles. For example, the interrogation conduit of each sensor 544, 548 may be sized in agreement with particles of a certain size. Tested sample fluid downstream of the MEMS chip then flows through channel extension 550 to waste chamber 552. Fluid flow may be urged by a vacuum 554 applied through a membrane 556.

Figure 33:
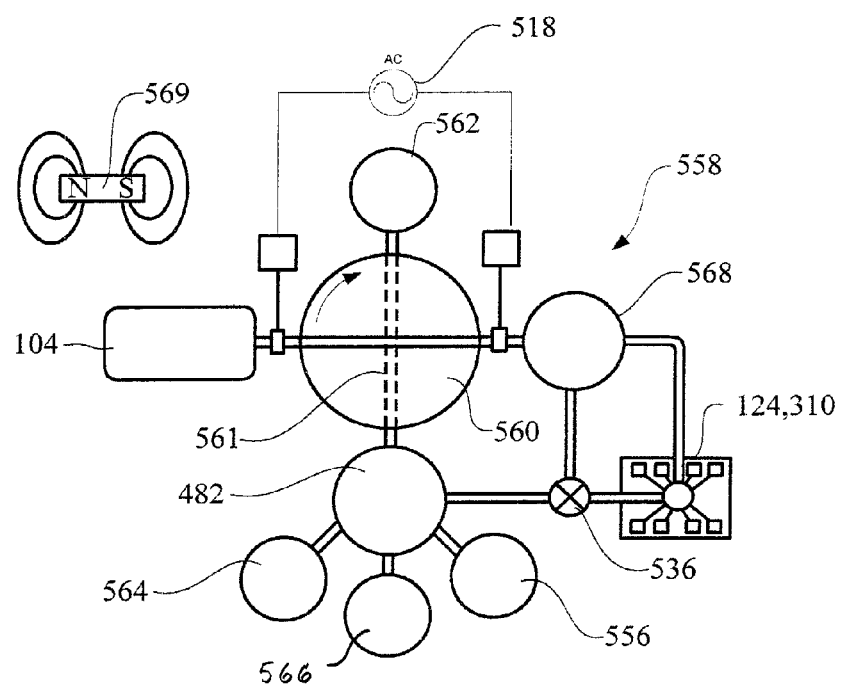
FIG. 33 is a plan view of structure carried by an embodiment of a cartridge according to certain aspects of the instant invention and operable selectively to permit flow of sample fluid for interrogation.

Structure desirably carried by a cartridge configured to perform a CD4+ test is generally indicated at 558 in FIG. 33. Structure 558 includes blood receiving structure or chamber 104, coupled to a fluid metering arrangement, such as indicated by valve 560. A bore 561 in valve 560 may be configured to contain, and thereby select, a desired known volume of sample fluid. A plurality of reagent chambers 562-566 desirably are disposed for introduction of reagents for sample manipulation. For example, in one useful configuration chamber 562 may contain solutions of latex or magnetic beads. Chambers 564 and 566 hold quantities of saline, and/or other fluids, for washing, treating, or diluting the test sample in mixing chamber 482. In general, reagent reservoirs may be adapted to dispense known quantities of fluids for selected sample manipulation. Fluid downstream of mix chamber 482 is directed for flow toward waste chamber 468, or through the MEMS chip 124, 310. As illustrated in FIG. 34, valve 536 may be associated with the mix chamber 482. An impedance monitor 518 desirably is included to ensure full charging of the metering valve 560 during introduction of the sample for a test. Structure to hold-back certain particles, such as magnet 569, is also desirably included in operable association with the cartridge.

The arrangement 558 may be used, in one nonlimiting example, as follows: A sample fluid is introduced to receiving structure 104, and drawn through metering valve 560 using a vacuum source 570 applied through a hydrophobic membrane 572 associated with waste chamber 568 (see FIG. 35). A low impedance measured by monitor 518 indicates when the valve 560 is fully charged, and air is removed in the fluid stretch disposed between its electrodes (and from the known-volume conduit 561). Valve 560 is then rotated, to the illustrated position, to permit reagent including antigen-bound latex beads from chamber 562 to flow and urge the selected volume of sample fluid to flow toward, and mix in, chamber 482. Latex monocyte blocking beads and fluid are used essentially to push the known volume of selected sample fluid into the mixing chamber. After the beads attach to the CD4 expressing monocytes, antigen-bound magnetic beads and solution is injected into chamber 482 from reagent chamber 574 and attach to the CD4 T cells, a magnetic field from magnet 569 can be applied on the mixing well to hold the bound cells in place during a first washing cycle using fluid from say, reservoir 564. A second washing cycle from say, reservoir 566, can resuspend the bound cells in the diluent "wash" media. Valve 536 is then adjusted to direct flow of the washed test sample through MEMS chip 124, 310 for counting.

In an alternative method for counting certain cells, after the known volume of blood is in the rotary chamber 561, and valve 560 is rotated 90 degrees, the known volume of blood is pushed into mixing chamber 482 using magnetic CD14 monocyte beads from chamber 562. After a brief incubation period (~5 minutes), an external magnetic source is turned on and CD4+ latex beads are injected into the mixing chamber 482 from one of the lower-illustrated reagent chambers (say chamber 564). In certain cases, it may be possible to inject the CD14 magnetic beads and the CD4 latex beads simultaneously from the same reservoir and then turn the magnetic source on. After another short incubation period, RBC lysing reagent is injected into the mixing chamber 482 from wash chamber (say from chamber 566) to lyse all the RBCs but not the WBCs. At this point, all of the WBCs are counted and the WBCs with the CD4+ latex beads attached (killer T cells) can be distinguished from regular WBCs because of their larger apparent diameter due to all of the small attached latex beads. This method provides both an absolute CD4 count and a WBC count. Such an alternative method may sometimes be used in milk WBC counting and human WBC counting with differential analysis.

Another method of use of certain embodiments of the invention encompasses removal of bubbles from a test sample. One such method includes the steps of: loading a sample of fluid into the cartridge; urging a quantity of the sample into the known volume selection chamber; monitoring the electric impedance through the known volume selection chamber to determine when the sample is bubble free; urging the known and air bubble free volume of test fluid to flow past the sensor for interrogation by the platform; and then, disposing of the cartridge. Variations on such bubble-free solution testing can be performed with or without electric impedance monitoring, mixing with diluent, etc.

While the invention has been described in particular with reference to certain illustrated embodiments, such is not intended to limit the scope of the invention. The present invention may be embodied in other specific forms without departing from its spirit or essential characteristics. The scope of the invention is, therefore, indicated by the appended claims. All changes which come within the meaning and range of equivalency of the claims are to be embraced within their scope.

What is claimed is:

1. A method for interrogating particles in a known volume of fluid using an electrical property-detecting sensor in a single-use, disposable cartridge with an interrogation platform structured to couple with the cartridge, the method comprising the steps of:

providing a single-use, disposable microfluidic test cartridge, comprising:
- a fluid receiving structure arranged to provide fluid communication of a fluid sample through a channel to a waste reservoir, said channel comprising an interrogation portion passing through a MEMS chip;
- a plurality of electrical contact pads that each are disposed in electrical communication with a selected electrode disposed in association with said interrogation portion;
- structure providing access to permit electrical coupling of an external device to said plurality of electrical contact pads;
- connection structure disposed in fluid communication with said channel and arranged to couple with an external fluid motive source effective to cause flow of at least a subset of said sample into said waste reservoir; and
- structure arranged to permit evacuation of air from said cartridge along a vent path while resisting escape of fluid from said cartridge along said vent path, at least a portion of said vent path being non-coaxial with said channel;

in combination with an interrogation platform, said platform comprising:
- alignment structure adapted to receive said cartridge in an installed substantially fixed interrogation orientation and to resist installation of said cartridge in another orientation;
- a plurality of electrical contacts individually configured for electrical coupling with a selected one of said plurality of electrical contact pads of an installed said cartridge;
- electronic interrogation circuitry adapted to apply an electric stimulation signal to one or more selected said electrical contacts and to receive a data signal from one or more of said electrical contacts and to output a modified signal for data analysis;
- a said fluid motive source configured to couple with said connection structure and operable to cause fluid flow through said channel; and
- biased retaining structure adapted to resist inadvertent removal of an installed said cartridge; and then a) loading a sample of fluid into said cartridge;

b) urging a quantity of said sample into a degassing chamber disposed along said channel and defining a known volume, said degassing chamber comprising a wall formed of hydrophobic material adapted to permit evacuation of entrained gas from said quantity while resisting escape of fluid from said degassing chamber therethrough to permit removal of bubbles from said quantity independently from urging motion of fluid from said degassing chamber and toward said waste reservoir; and applying a reduced pressure, compared to a pressure inside said degassing chamber, through said vent path and to a portion of said wall outside of said degassing chamber for a period of time sufficient to permit migration of gas bubbles from said quantity through said wall to form a known and degassed volume of test fluid;

c) urging said volume of sample fluid to flow past said sensor for interrogation by said platform; and d) disposing of said cartridge.

2. A method for performing a serial analysis on first and second subsets of particles in a fluid sample using an electrical property sensor housed in a single-use, disposable cartridge with an interrogation platform structured to couple with the cartridge, the method comprising the steps of:

providing a single-use, disposable microfluidic test cartridge, comprising:
- a fluid receiving structure arranged to provide fluid communication of said fluid sample through a channel to a waste reservoir, said channel comprising an interrogation portion passing through a MEMS chip;
- a plurality of electrical contact pads that each are disposed in electrical communication with a selected electrode disposed in association with said interrogation portion;
- structure providing access to permit electrical coupling of an external device to said plurality of electrical contact pads;
- connection structure disposed in fluid communication with said channel and arranged to couple with an external fluid motive source; and
- structure arranged to permit evacuation of air from said cartridge along a vent path while resisting escape of fluid from said cartridge along said vent path, at least a portion of said vent path being non-coaxial with said channel;

in combination with an interrogation platform, said platform comprising:
- alignment structure adapted to receive said cartridge in an installed substantially fixed interrogation orientation and to resist installation of said cartridge in another orientation;
- a plurality of electrical contacts individually configured for electrical coupling with a selected one of said plurality of electrical contact pads of an installed said cartridge;
- electronic interrogation circuitry adapted to apply an electric stimulation signal to one or more selected said electrical contacts and to receive a data signal from one or more of said electrical contacts and to output a modified signal for data analysis;
- a said fluid motive source configured to couple with said connection structure and operable to cause fluid flow through said channel; and
- biased retaining structure adapted to resist inadvertent removal of an installed said cartridge; and then a) loading a sample of fluid into said cartridge;

b) urging a quantity of said sample into a mixing chamber disposed at an intermediate position along said channel in said cartridge;

c) applying one or more reagent to said quantity effective to form at least two subsets of particles;

d) applying a force effective to restrain movement of a first subset of particles from said mixing chamber;

e) urging a second subset of particles to flow past said sensor for interrogation by said platform;

f) subsequently urging said first subset of particles to flow past a sensor for interrogation by said platform; and g) disposing of said cartridge.

3. The method according to claim 2, wherein:

said sample comprises whole blood;

step c) comprises mixing a quantity of antigen-bound magnetic beads with said sample operably to bind said beads to certain white blood cells; and step d) comprises applying a magnetic field to said magnetic beads.

4. The method according to claim 3, wherein:

step f) comprises adjusting structure associated with said cartridge to cause flow of said first subset for analysis through a second sensor that is differently structured from said first sensor.

5. The method according to claim 2, wherein:

said card further comprises a degassing chamber associated with said mixing chamber, said degassing chamber comprising a wall formed of hydrophobic material adapted and arranged to permit evacuation, through said vent path, of entrained gas from a portion of said sample while resisting escape of fluid from said degassing chamber therethrough to permit removal of bubbles from said portion of said sample independently from urging motion of fluid from said degassing chamber and toward said waste reservoir.

6. A method for particle analysis, comprising the steps of:

a) providing a particle detector capable of detecting particles entrained in a fluid based upon interrogation of electrical impedance through a portion of said fluid;

b) providing a one-time use cartridge structured according to claim 1 and configured and arranged to cooperate with said detector effective to permit interrogation, by said detector, of particles entrained in a fluid sample carried by said cartridge;

c) applying a quantity of antibody bound beads to a portion of said fluid sample to permit binding of beads to receptive particles; and d) operating said detector to perform said analysis.

7. The method according to claim 6, wherein:

step c) comprises applying a quantity of antibody bound latex beads effective to form a first population of bound particles having a larger particle size in combination than a second population of unbound particles; and step d) comprises operating said detector to characterize at least one of said first population and said second population.

8. The method according to claim 6, wherein:

step c) comprises:

i) applying a quantity of antibody hound magnetic beads effective to form a first population of bound particles having a different magnetic property in combination compared to a second population of unbound particles; and ii) applying a magnetic field to resist movement of said first population while separating said second population from said first population; and step d) comprises operating said detector to characterize at least one of said first population and said second population.

9. A method for interrogating particles in a known volume of fluid using an electrical property-detecting sensor in a disposable cartridge with an interrogation platform structured to couple with the cartridge, the method comprising the steps of:

providing a disposable microfluidic test cartridge, comprising:

a fluid receiving structure arranged to provide fluid communication of a fluid sample through a channel to a reservoir in which to receive processed fluid, said channel comprising an interrogation portion passing through a MEMS chip;

a plurality of electrical contact pads, certain of said contact pads being disposed in electrical communication with one or more cooperating electrode disposed in said interrogation portion effective to permit electronic interrogation circuitry of said interrogation platform to apply an electric stimulation signal to one or more selected electrical contact pads and to receive a data signal from one or more of said electrical contact pads and to output a modified signal for data analysis;

structure providing access to permit electrical coupling of said interrogation platform to said plurality of electrical contact pads;

connection structure disposed in fluid communication with said channel and arranged to couple with a fluid motive source effective to cause flow of at least a subset of said fluid sample into said reservoir; and structure arranged to permit evacuation of air from said cartridge along a vent path, at least a portion of said vent path being non-coaxial with said channel;

alignment structure adapted to couple said cartridge with said interrogation platform to locate said cartridge in an installed substantially fixed interrogation orientation and to resist installation of said cartridge in another orientation; and then a) loading a sample of fluid into said cartridge;

b) urging a quantity of said sample into a degassing chamber disposed along said channel and defining a known volume, said degassing chamber comprising a wall formed of hydrophobic material adapted to permit evacuation of entrained gas from said quantity while resisting escape of fluid from said degassing chamber therethrough to permit removal of bubbles from said quantity independently from urging motion of fluid from said degassing chamber and toward said reservoir; and applying a reduced pressure, compared to a pressure inside said degassing chamber, through said vent path and to a portion of said wall outside of said degassing chamber for a period of time sufficient to permit migration of gas bubbles from said quantity through said wall to form a known and degassed volume of test fluid;

c) urging said volume of sample fluid to flow past said sensor for interrogation by said platform; and d) disposing of said cartridge.

10. The method according to claim 9, wherein:

said cartridge is adapted for only a single-use prior to disposal.

* * * * *